(12) United States Patent
Hermel-Davidock et al.

(10) Patent No.: US 10,806,829 B2
(45) Date of Patent: *Oct. 20, 2020

(54) ANTIMICROBIAL MEDICAL DEVICES

(71) Applicant: Becton, Dickinson and Company, Franklin Lakes, NJ (US)

(72) Inventors: Theresa Hermel-Davidock, Vernon Hills, IL (US); Tea Datashvili, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/104,442

(22) Filed: Aug. 17, 2018

(65) Prior Publication Data

US 2019/0054213 A1    Feb. 21, 2019

Related U.S. Application Data

(60) Provisional application No. 62/547,167, filed on Aug. 18, 2017, provisional application No. 62/684,946, filed on Jun. 14, 2018, provisional application No. 62/715,868, filed on Aug. 8, 2018.

(51) Int. Cl.
| | |
|---|---|
| *C08F 255/02* | (2006.01) |
| *C08F 210/06* | (2006.01) |
| *C08L 23/12* | (2006.01) |
| *C08L 51/06* | (2006.01) |
| *C08L 51/00* | (2006.01) |
| *C08L 23/10* | (2006.01) |
| *C08L 23/14* | (2006.01) |
| *A61L 29/04* | (2006.01) |
| *C09C 1/30* | (2006.01) |
| *A01N 25/10* | (2006.01) |
| *A01N 43/40* | (2006.01) |
| *A01N 43/90* | (2006.01) |
| *A01N 59/16* | (2006.01) |
| *A01N 59/20* | (2006.01) |
| *A61K 31/44* | (2006.01) |
| *A61K 31/4745* | (2006.01) |
| *A61K 33/34* | (2006.01) |
| *A61K 33/38* | (2006.01) |
| *A61K 47/32* | (2006.01) |
| *A61L 29/16* | (2006.01) |

(52) U.S. Cl.
CPC ............ *A61L 29/041* (2013.01); *A01N 25/10* (2013.01); *A01N 43/40* (2013.01); *A01N 43/90* (2013.01); *A01N 59/16* (2013.01); *A01N 59/20* (2013.01); *A61K 31/44* (2013.01); *A61K 31/4745* (2013.01); *A61K 33/34* (2013.01); *A61K 33/38* (2013.01); *A61K 47/32* (2013.01); *A61L 29/16* (2013.01); *C08F 210/06* (2013.01); *C08F 255/02* (2013.01); *C08L 23/12* (2013.01); *C08L 51/06* (2013.01); *C09C 1/30* (2013.01); *C09C 1/309* (2013.01); *A61L 2300/404* (2013.01)

(58) Field of Classification Search
CPC .......... C08L 23/12; C08L 51/06; C08L 23/14; C08L 23/10; C08F 255/02; C08F 210/06; C08F 110/06
See application file for complete search history.

(56) References Cited

U.S. PATENT DOCUMENTS

| | | | |
|---|---|---|---|
| 4,959,406 A | 9/1990 | Foltin et al. | |
| 5,735,830 A * | 4/1998 | Fritz | A61L 29/041 |
| | | | 604/523 |
| 5,910,523 A | 6/1999 | Hudson | |
| 8,911,658 B2 | 12/2014 | Jiang | |
| 2003/0018306 A1 * | 1/2003 | Bucay-Couto | A61L 27/34 |
| | | | 604/265 |

(Continued)

FOREIGN PATENT DOCUMENTS

| | | | |
|---|---|---|---|
| CN | 106674750 A | 5/2017 | |
| WO | WO-2008027720 A2 * | 3/2008 | ........... A61L 31/088 |

OTHER PUBLICATIONS

Viet et al. Preparation of antibacterial polypropylene grafted acrylic acid and immobilized silver nanoparticles by gamma-irradiation method. (2016). Journal of Biotechnology. vol. 14. Issue 4. pp. 699-704. (Year: 2016).*

(Continued)

*Primary Examiner* — Tracy Liu
(74) *Attorney, Agent, or Firm* — Servilla Whitney LLC

(57) ABSTRACT

Medical devices comprise a polymeric body comprising: a base polymeric formulation comprising at least a polymer or co-polymer of propylene; and an additive comprising a copolymer having a polypropylene backbone and hybrid micromolecule side-chains based on organo-functional silanes (PP-g-XSiOA) in the presence of a co-agent, for example, difunctional metallic diacrylate monomers, where "X" is an organic group or an organo-functional group, and "A" is a metal, an inorganic oxide, an inorganic hydroxide, or any other inorganic material. X may be derived from a compound selected from the group consisting of epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing. Antimicrobial agents are included in the polymeric body. The medical devices have enhanced antimicrobial properties.

17 Claims, 11 Drawing Sheets

(56) References Cited

U.S. PATENT DOCUMENTS

2004/0071994 A1 4/2004 Busch et al.
2007/0244284 A1* 10/2007 Cheng .................... A61L 27/34
526/319

OTHER PUBLICATIONS

PCT International Search Report and Written Opinion in PCT/US2018/046941, dated Dec. 7, 2018, 15 pages.
PCT International Search Report and Written Opinion in PCT/US2018/046948, dated Dec. 7, 2018, 16 pages.
PCT International Search Report and Written Opinion PCT/US2018/046946, dated Dec. 7, 2018, 17 pages.
Bailly, Mathieu, et al., "Preparation and characterization of thermoplastic olefin/nanosilica composites using a silane-grafted polypropylene matrix", Elsevier Ltd., Mar. 20, 2009, 2472-2480.
Bauer, Frank, et al., "Preparation of Scratch and Abrasion Resistant Polymeric Nanocomposites by Monomer Grafting onto Nanoparticles, 3a Effect of Filler Particles and Grafting Agents", Macromolecular Materials and Engineering, Jan. 22, 2002, 546-552.
Hasse, Andre, et al., "Reinforcement of Silica-Filled EPM Compounds using Vinylsilanes", Applied Technology Advanced Fillers, 1-6.
Sherman, Lilli Manolis, "Laser Marking Has a Bright Future in Plastics", Plastics Technology, Aug. 1, 2001, 52.
Shin-Etsu Chemical Co., Ltd., "Silane Coupling Agents", Shin-Etsu Chemical Co., Ltd., Jun. 2017, 1-28.
Non-Final Office Action in U.S. Appl. No. 16/104,436, dated Mar. 2, 2020, 17 pages.
Bailly, Mathieu, et al., "Preparation and characterization of thermoplastic olefin/nanosilica composites using a ilane-grafted polypropylene matrix", Polymer 50, Mar. 20, 2009, 2472-2480.

* cited by examiner

ANTIMICROBIAL MEDICAL DEVICES

CROSS-REFERENCE TO RELATED APPLICATIONS

This application claims priority under 35 U.S.C. § 119(e) to U.S. Provisional Application No. 62/547,167, filed Aug. 18, 2017, and U.S. Provisional Application No. 62/684,946, filed Jun. 14, 2018, and U.S. Provisional Application No. 62/715,868, filed Aug. 8, 2018, the disclosures of which are incorporated herein by reference in their entireties.

TECHNICAL FIELD

Principles and embodiments of the present invention relate generally to medical devices including amphiphilic graft copolymers in combination with one or more antimicrobial agents. The amphiphilic graft copolymers are functionalized polypropylene copolymers. Hybrid inorganic-organic micromolecules are copolymerized with polypropylene in the presence of a co-agent, for example, difunctional metallic diacrylate monomers. The polypropylene-based graft copolymers have a polypropylene backbone and hybrid micromolecule side-chains, which are based on organo-functional silanes and an inorganic portion (PP-g-XSiOA), where "X" is an organic group or an organo-functional group, and "A" is a metal, an inorganic oxide, an inorganic hydroxide, or any other inorganic material. Including PP-g-XSiOA in combination with antimicrobial agents in formulations of propylene-containing polyolefin or thermoplastic elastomer (TPE) which are utilized in making medical devices allows the devices to have enhanced antimicrobial properties.

BACKGROUND

Medical devices are commonly made from polyolefin (e.g., ethylene-or propylene-containing) or thermoplastic elastomer (TPE) materials. Functional properties can be incorporated into known polymers to provide desired traits. U.S. Pat. No. 9,150,674 is directed to amphiphilic graft copolymers involving grafting either poly(ethylene oxide) or polylactide side chains onto known polymers, such as poly(ethylene-co-vinyl acetate) or maleic anhydride-grafted polypropylene.

Polypropylene (PP) and polypropylene based materials (PPBMs) such as thermoplastic olefins (TPO) or thermoplastic elastomer (TPE) compounds are popular materials among other plastics. Excellent chemical and heat resistance, ease of process, low scrap rates, and recyclability have earned PPBMs a market niche that continues to expand in the medical applications. PPBMs are considered viable candidates in medical tubing, drug storage, delivery devices, face masks, smart packaging and infant-care items applications where clarity, sterilization, and low extractables as well as bondability to a range of engineering thermoplastics and metal surfaces are highly desired. However, PPs and PPBMs are non-polar (absence of hydrophilic groups) and do not contain reactive functional groups that limits there applications in the fields where adhesion, solvent bondability, surface paintability, laser marking or dispersion of the polar additives (reinforcement, modifier or antimicrobial agents) are highly desired.

Antimicrobial polymer-based materials have been developed using antimicrobial additives. Compatibility and dispersion issues between additives and polymer matrixes, however, significantly decreases antimicrobial activity of the additives, and also makes controlling the antimicrobial agent release rate challenging. Incompatibility issues can lead to consumption of high amounts of antimicrobial additives to achieve antimicrobial properties. Addition of high amounts of additives can improve antimicrobial properties but at the same time can cause significant changes in physical, mechanical properties, and rheology behavior of the polymer. Changes in polymer properties can limit utilization of materials in applications where good antimicrobial and mechanical-rheological property balance is desired. Developing polymer-based materials with good antimicrobial properties while maintaining mechanical-rheology properties of the polymer is challenging.

There is a need to develop polypropylene and PPBMs that include antimicrobial agents and have enhanced antimicrobial properties.

SUMMARY

Provided are medical devices including amphiphilic graft copolymers based on a polypropylene backbone and hybrid micromolecule side-chains based on organo-functional silanes and an inorganic portion in the presence of a co-agent, for example, difunctional metallic diacrylate monomers. The amphiphilic graft copolymers are functionalized polypropylene copolymers, which may be in accordance with commonly-owned U.S. Ser. No. 62/547,167 filed Aug. 18, 2017, hereby incorporated by reference in its entirety. The graft copolymers are co-blended with base formulations in order to form medical devices by injection molding or by extrusion. The medical devices herein have enhanced antimicrobial properties.

In an aspect, medical device comprises: a polymeric body comprising: a base polymeric formulation comprising at least a polymer or co-polymer of propylene; and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; the PP-g-XSiOA being in a blend with the base polymeric formulation in an amount in the range of about 0.01 to about 20.0% by weight of the blend; and an antimicrobial agent.

The antimicrobial agent may comprise: berberine chloride, berberine chloride hydrate, octinedine dihydrochloride, 4-chlorophenyl methyl sulfone, climbazole, piroctone olamine, silver sulfadiazine, copper particles, silver particles, or combinations thereof. The antimicrobial agent may be present in an amount in the range of 0.02 to 3% by weight of the blend of additive and base polymeric formulation.

The base polymeric formulation may comprise polypropylene, a polyethylene-polypropylene co-polymer, a polypropylene-containing thermoplastic elastomer (TPE), or combinations thereof.

In one or more embodiments, the medical device is tubing or barrel or any other component of medical device.

The PP-g-XSiOA may be an amphiphilic copolymer comprising polypropylene and an inorganic-organic hybrid micromolecule, which is according to Formula (I):

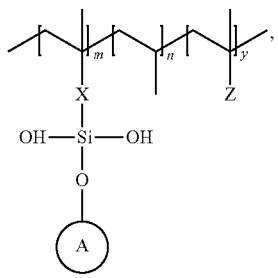

(I)

wherein X is an organic or an organo-functional group containing 1 to 6 carbons; A is a metal, an inorganic oxide, an inorganic hydroxide, or any other inorganic material; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X$_2$; XSiOR; or XSiOH, wherein "M-X$_2$" is an organo-metal salt and "OR" is an alkoxy group having 1 to 4 carbons.

The inorganic-organic hybrid micromolecule may be a reaction product of an organo-silane and an inorganic oxide and/or hydroxide.

X of the PP-g-XSiOA may be derived from a compound selected from the group consisting of epoxy, amino, acrylate, methacryloxy, and vinyl; and A may be selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

The inorganic-organic hybrid micromolecule grafted to the polypropylene may be a reaction product of an organo-functional silane with an inorganic oxide and/or hydroxide in solution, wherein a weight ratio of the organo-functional silane to the inorganic oxide and/or hydroxide is at least 10:1.

In an embodiment, where y is 0, the amphiphilic copolymer is according to Formula (IA):

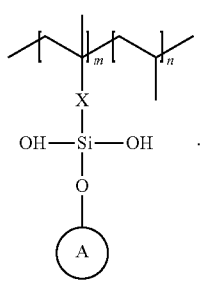

(IA)

In an embodiment, when X is derived from 3-(trimethoxysilyl)propyl methacrylate, the amphiphilic copolymer is according to Formula (VII):

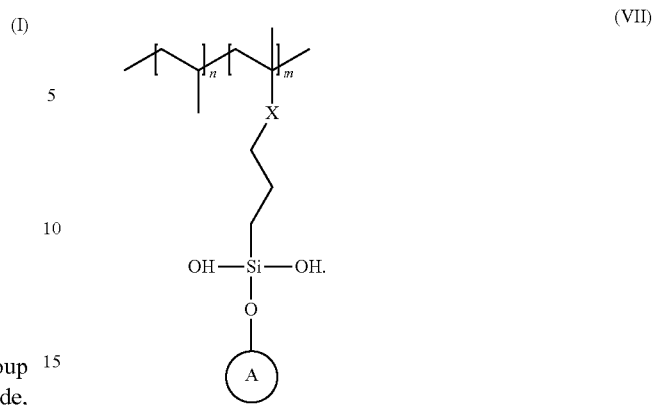

(VII)

In one or more embodiments, A may be derived from Si(OH)$_4$ or SiO$_2$.

The amphiphilic copolymer may have a melting point in the range of 140 to 180° C. The amphiphilic copolymer may have a capillary viscosity in the range of 100 to 300 Pa·s at 180 s$^{-1}$. The amphiphilic copolymer may have a weight average molecular weight (Mw) in the range of about 100,000 to about 350,000 g/mol. The amphiphilic copolymer may have a dispersity index in the range of 1.5 to 9. The amphiphilic copolymer may have a long chain branching frequency in the range of 0.007 to 0.017 per 1000 carbon. The amphiphilic copolymer may have a melt flow rate in the range of 15 to 55 g/10 minutes.

A further aspect is a method of making a medical device that comprises obtaining a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; combining the PP-g-XSiOA with a base polymeric formulation comprising at least a polymer or co-polymer of propylene to form a blend, the PP-g-XSiOA being present in the blend in an amount in the range of about 0.01 to about 20.0% by weight of the blend; adding an antimicrobial agent to the blend to form a mixture; and forming a polymeric body from the mixture. The antimicrobial agent may comprise: berberine chloride, berberine chloride hydrate, octinedine dihydrochloride, 4-chlorophenyl methyl sulfone, climbazole, piroctone olamine, silver sulfadiazine, copper particles, silver particles, or combinations thereof.

The base polymeric formulation may comprise polypropylene, a polyethylene-polypropylene co-polymer, a polypropylene-containing thermoplastic elastomer (TPE), or combinations thereof.

The PP-g-XSiOA may be according to Formula (I). The X of the PP-g-XSiOA may be derived from a compound selected from the group consisting of epoxy, amino, acrylate, methacryloxy, and vinyl; and A may be selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

The PP-g-XSiOA may have a melting point in the range of 140 to 180° C. The PP-g-XSiOA may have a capillary viscosity in the range of 100 to 300 Pa·s at 180 s$^{-1}$. The PP-g-XSiOA may have a weight average molecular weight (Mw) in the range of about 100,000 to about 350,000 g/mol. The PP-g-XSiOA may have a dispersity index in the range of 1.5 to 9. The PP-g-XSiOA may have a long chain branching frequency in the range of 0.007 to 0.017 per 1000 carbon. The PP-g-XSiOA may have a melt flow rate in the range of 15 to 55 g/10 minutes. In one or more embodiments, at least a portion of the polymeric body is transparent. In one or more embodiments, the medical is device is in the form of tubing, barrel, rod, or any other geometric shape.

DETAILED DESCRIPTION

Figure 1:
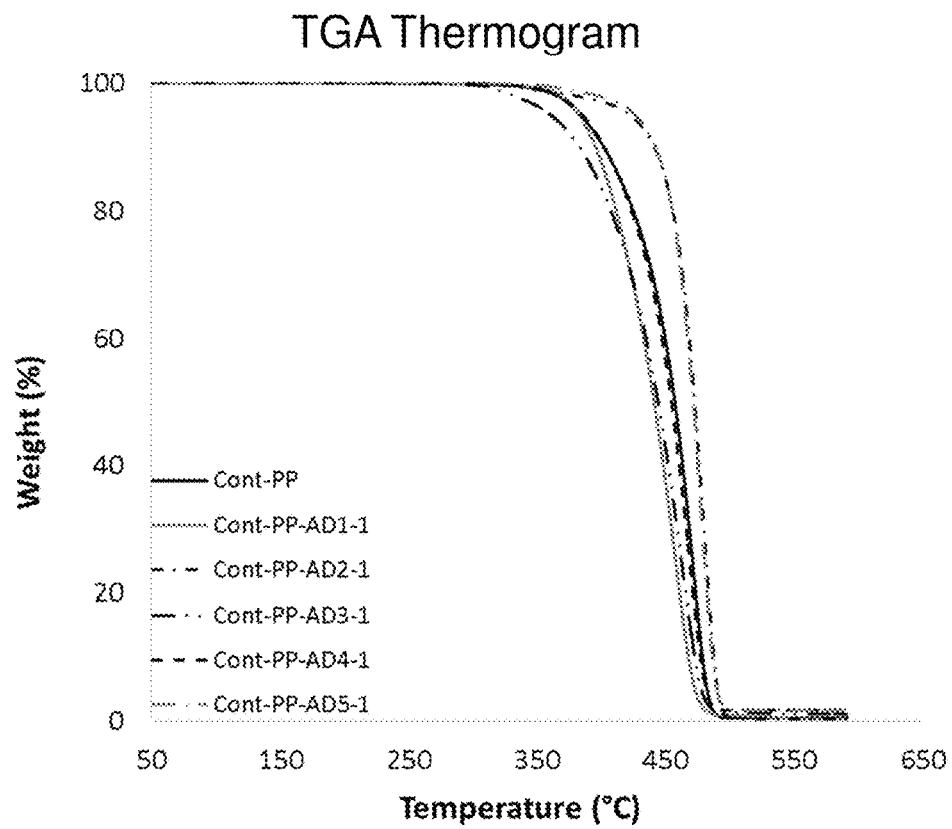
FIG. 1 provides a thermogram from thermogravimetric analysis (TGA). TGA curve of weight % versus temperature (° C.) for control compositions: Group 1 "Cont-PP" and Group 2 of Table 3.

Before describing several exemplary embodiments of the invention, it is to be understood that the invention is not limited to the details of construction or process steps set forth in the following description. The invention is capable of other embodiments and of being practiced or being carried out in various ways.

The present disclosure provides polypropylene (PP) and polypropylene based materials (PPBMs) that provide antimicrobial properties. Medical devices disclosed herein address antimicrobial properties needs of polymeric materials for healthcare applications while maintaining mechanical-rheology properties of the polymer by using amphiphilic graft copolymers in combination antimicrobial agents in medical devices made from PP and PP-based polymeric materials (including PP based thermoplastic elastomers (TPE)). Antimicrobial agents include but are not limited to: berberine chloride, berberine chloride hydrate, octinedine dihydrochloride, 4-chlorophenyl methyl sulfone, climbazole, piroctone olamine, silver sulfadiazine, copper particles, silver particles, and combinations thereof.

The amphiphilic graft copolymers include organic hybrid micromolecule side-chains based on organo-functional silanes chemistry in a polypropylene backbone in the presence of a co-agent, for example, difunctional metallic diacrylate monomers. The amphiphilic graft copolymers can be used as a single component system or as an additive for thermoplastic elastomers to promote antimicrobial properties. Advantageously, the introduction of amphiphilic groups into PP chain as well as to reinforce PP matrix by grafting hybrid micromolecules promotes antimicrobial properties.

Modified PP and PPBMs can be beneficially used in making parts of the medical devices including, but not limited to balloon catheters; tubing for feeding, drainage, and use with peristaltic pumps; compression bars; electrosurgical hand pieces; infusion sleeves and test chambers; introducer tips and flexible sheaths; ear plugs and hearing aids; shunts and septums; and a variety of seals, stoppers, valves, and clips; as well as for applications such as IV tubing, catheter extension set tubing and catheter tubing. The presence of organic hybrid micromolecules in the polymer (e.g., polypropylene) increases affinity of the polymer matrix with antimicrobial agents, achieves antimicrobial properties at low concentration levels and improves antimicrobial agent release rate. This phenomena can be explained by unique nature of amphiphilic copolymers which are acting as compatibilizer agents between polymers and inorganic additives and thus achieving good antimicrobial performance of polymer at low concentration level of the antimicrobial additives via homogeneous dispersion and improved interactions (adhesion) with the polymer matrix.

PP-based amphiphilic graft copolymers are obtained via modification technology disclosed in commonly-owned U.S. Ser. No. 62/547,167 filed Aug. 18, 2017, hereby incorporated by reference in its entirety. Chemistry and subsequently hydrophilicity of PP and/or PP-based materials are changed by incorporating functional groups based on hybrid organic silane micromolecules in combination with the difunctional metallic diacrylate monomers.

Principles and embodiments of the present invention relate to medical devices including amphiphilic graft copolymers in combination with antimicrobial agents. The amphiphilic graft copolymers are based on chemical modification of commodity polypropylene via a chemical grafting.

SYNTHESIS OF FUNCTIONALIZED-PP

The amphiphilic polypropylene-based graft copolymers combine hybrid inorganic-organic micromolecules with polypropylene in the presence of a co-agent. The copolymers are in accordance with Formula (I):

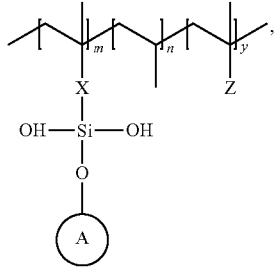
(I)

wherein "X" is an organic or an organo-functional group containing 1 to 6 carbons, "A" is a metal, an inorganic oxide, an inorganic hydroxide, or any other inorganic material, "n" is an integer that is in excess of 100, "m" is an integer that is 1 or greater, and "y" is 0 or a number greater than 0. X is derived from X', which is an organo-functional group containing 1 to 6 carbons, whose functionality includes a reactive group suitable for radical polymerization. The integer n is a very large number, and can represent hundreds or thousands of repeating units in one molecule. In one or more embodiments, n is an integer in the range of 100 to 1,000,000; or 500 to 750,000; or 1,000 to 500,000; and all values and subranges therebetween. Reference to "n" is with respect to propylene units, "m" is to grafted hybrid side chains, and "y" is to grafted secondary side chains ("Z"). The molar value of "m" is in the range of about 0.1 to 20 mole percent, the molar value of "y" is in the range of about 0 to 2.0 mole percent, and the molar value of "n" is in the range of about 78 to 99.9 mole percent. "Z", when y is greater than 0, comprises a secondary side chain: M-$X_2$; XSiOR; or XSiOH, wherein "M-$X_2$" is an organo-metal salt, "OR" is an alkoxy group having 1 to 4 carbons.

When "y" is 0, Formula (I) becomes Formula (IA):

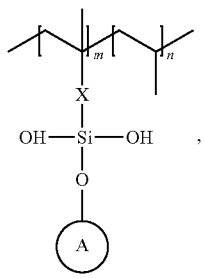
(IA)

In a first step, hybrid inorganic-organic micromolecules (AOSiX') are either synthesized in solution or commercially obtained. The hybrid micromolecules are effective to deliver desirable functionality to the copolymers when their grafting degree with respect to the polypropylene backbone is at least 0.1 mol. % of the amphiphilic copolymer (e.g., n is >=0.1 mol. %). The targeted hybrid micromolecules are according to general formula (II):

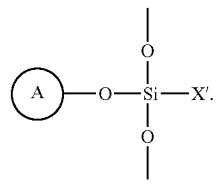
(II)

"X'" is an organo-functional group containing 1 to 6 carbons, whose functionality includes a reactive group suitable for radical polymerization. Reactive groups suitable for radical polymerization include, for example, ethylenically unsaturated groups, epoxies, acrylates and amines.

During synthesis of hybrid inorganic-organic micromolecules, secondary micromolecules may result from side reactions, $(OH)_3SiX'$, and incomplete hydrolysis reactions, $(OR)_3SiX'$.

Hybrid micromolecules may be generated by treating a precursor of "A". The precursors are inorganic materials including but not limited to inorganic oxides, inorganic hydroxides, and any inorganic materials with one or more surface hydroxyl groups on the surface, with "X'SiO", which is an organo-functional silane.

Inorganic materials, "A", which are the inorganic portion of the hybrid inorganic-organic micromolecules, may include but are not limited to one or more of the following: a metal, an inorganic oxide, an inorganic hydroxide, or any other inorganic material. In an embodiment, A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing. The precursor of "A" reacts by hydrolysis with one or more the organo-functional silanes having an ethylenically unsaturated group. A may be derived from, for example, $Si(OH)_4$ or $SiO_2$.

Organo-functional silanes, X'SiO, which are the organic portion of the hybrid inorganic-organic micromolecules, may be according to general formula (IV):

$$X'—Si(OR)_3 \qquad (IV),$$

wherein "OR" is an alkoxy group having 1 to 4 carbons, and "X'" is an organo-functional group, containing at least one reactive group suitable for radical polymerization. The organo-silanes thus contain two different types of reactive groups: the OR groups, which are easily hydrolysable groups such as methoxy or ethoxy groups suitable for hybrid inorganic-organic micromolecules (AOSiX') synthesis; and the X' group, which is an organo-functional group such as epoxy, amino, acrylate, methacryloxy, or vinyl suitable for radical polymerization. The inorganic-organic hybrid micromolecule is therefore a reaction product of an organo-silane and an inorganic oxide and/or hydroxide.

Si—OR bonds hydrolyze readily with water (even if only moisture adsorbed on the surface) to form Si—OH groups. Si—OR bonds can also be readily condense with hydroxyl groups on the surface of inorganic oxides, hydroxides, minerals or metals to form stable Si—O-A bonds (A=Si, Al, Fe, and the like) thus hybrid micromolecules are formed through hydrolysis, condensation process that takes place between organo-functional silane micromolecules and the hydroxide groups of the inorganic materials (fillers).

Hybrid materials may be synthesized at room temperature by dispersing the precursor of "A", e.g., inorganic oxide or hydroxide powder, in an organo-functional silane solution, wherein a weight ratio of the organo-functional silane group to precursor is at least 10:1. That is, in one or more embodiments, the amount of the organo-functional silane group to precursor is at least 10 times that of precursor to achieve completion of hybrid materials synthesis. In one or more embodiments, the weight ratio of organo-functional silane to the inorganic oxide or hydroxide precursor to is in the range of 10:1 to 1000:1. The dispersion is then ultrasonicated for at least 3 hours to form targeted hybrid micromolecules are according to general formula (II).

An exemplary hybrid material may be formed using a silicon dioxide ($SiO_2$) and 3-(trimethoxysilyl)propyl methacrylate according to equation (a-1):

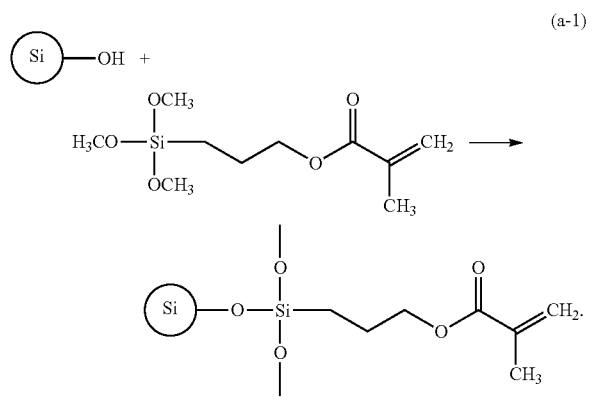

wherein 3-(trimethoxysilyl)propyl methacrylate is a precursor with tri methoxy groups. Degree of functionality of hybrid material may be monitored by FTIR and 1H-NMR; for example for 3-(trimethoxysilyl)propyl methacrylate based hybrid micromolecules functionality is measured by monitoring formation of characteristic carbonyl (C=O) stretching vibration at 1500-1750 $cm^{-1}$ FTIR range (see FIG. 9).

Silicones (polysiloxanes) are an exemplary group of inorganic-organic hybrid compounds, composed of silicon and oxygen atoms in the main chains and organic substituents bound to silicon. Silicones are mainly applied as silicone oils, rubbers, and they are also used to modify polymer properties. In addition to silicones, reactive silanes, siloxanes, and silicates, are also used for the modification of polymer properties. Silane used in this invention is commercially available from the Mitsubishi Corporation, Evonik and the Struktol.

Functional organosilanes suitable for use in this process include, but are not limited to, tetraethoxysilane, methyltrimethoxysilane, methyltriethoxysilane, dimethyldimethoxysilane, propyltrimethoxysilane, propyltriethoxysilane, iso-butyltrimethoxysilane, iso-butyltriethoxysilane, phenyltrimethoxysilane, n-octyltriethoxysilane, methacryloxypropyltrimethoxysilane, chloropropyltriethoxysilane, methyldimethoxysilane, phenyltriethoxysilane, chloropropyltrimethoxysilane, aminoethylaminopropyltrimethoxysilane, glycidoxypropyltrimethoxysilane, vinyltriethoxysilane, tetraethoxysilane, (3-acetamidopropyl)trimethoxysilane, acetoxyethyldimethylchlorosilane, acetoxyethylmethyldichlorosilane, acetoxyethyltrichlorosilane, acetoxyethyltriethoxysilane, acetoxyethyltrimethoxysilane, acetoxyethyltris(dimethylamino)silane, acryloxymethyltrimethysilane, allyltrichlorosilane, allyltriethoxysilane, allyltri-iso-propylsilane, allyldimethylchlorosilane, allylmethyldichlorosilane, allylmethyldimethoxysilane, allyltrimethoxysilane, allylphenyldichlorosilane, 3-acrylamidopropyltris(trimethylsiloxy)silane.

During polymerization, a free-radical initiator is present. Peroxide-based free-radical initiators are preferred, specifically organic peroxides. Exemplary organic peroxides include but are not limited to, cyclic peroxides, diacyl peroxides, dialkyl peroxides, hydroperoxides, peroxycarbonates, peroxydicarbonates, peroxyesters, peroxyketals, and mixtures thereof.

Exemplary peroxides include: dihexylene glycol peroxide; 4-(t-hexylperoxy)-4-methyl-2-pentanol; 4-(t-octylperoxy)-4-methyl-2-pentanol; 2-methyl-2-t-amylperoxy-4-pentanone; di-t-hexyl peroxide; di-t-octyl peroxide; the t-amyl, t-hexyl and t-octyl analogs of LUPEROX 101; analogs of Perkadox 24L (dicetyl peroxydicarbonate) and Perkadox 16; mixed dialkyl peroxides such as t-amyl-t-hexyl peroxide and t-amyl-t-octyl peroxide.

An exemplary free-radical initiator is 2,5-bis(tert-butylperoxy)-2,5-dimethylhexane, which is sold under the tradename LUPEROX 101, according to formula (V):

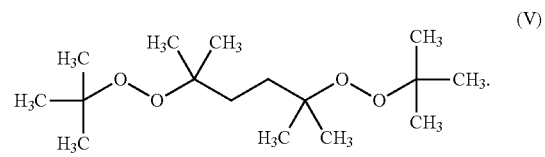 [SMILES: CC(C)(C)OOC(C)(C)CCC(C)(C)OOC(C)(C)C]

The grafting reaction of hybrid side chains onto a polypropylene (PP) backbone proceeds according to equations (b) to (c). As a starting polymer, commercially available polypropylene homopolymers can be used with melt values in the range of 0.5-20 g/10 minutes.

In a first step according to equation (b), there is free radical formation by thermal decomposition of organic peroxide and formation of the macro radical.

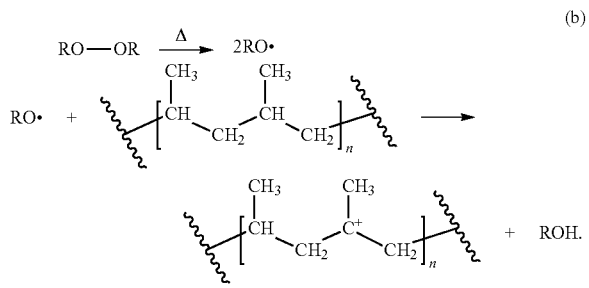

In a second step according to (c), there is grafting of hybrid micromolecules according to general formula (II) onto the polypropylene chain.

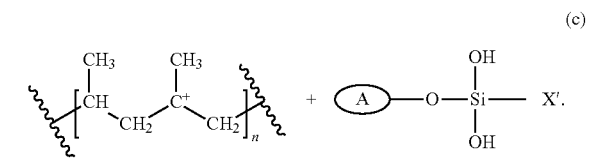

wherein A is a metal, an inorganic oxide, an inorganic hydroxide, or any other inorganic material and X' is a group selected from: epoxy, amino, acrylate, methacryloxy, and vinyl.

For the specific hybrid micromolecules obtained by equation (a-1), and accounting for possible secondary reactions during hybrid synthesis (X'SiOR and X'SiOH), the amphiphilic copolymer is according to (VI).

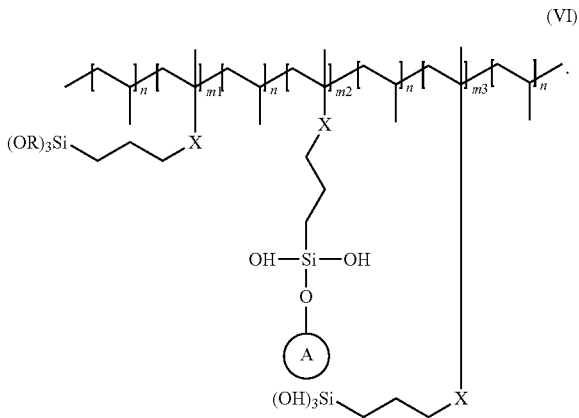

wherein the molar value of "$m_1+m_2+m_3$" is in the range from 0.1 to 20 mole percent; and the molar value of "n" is in the range from 80 to 99.9 mole percent. When $m_1$ and $m_3$ are 0 or the secondary chains are negligible, the amphiphilic copolymer when using the hybrid of (a-1) has a structure according to (VII):

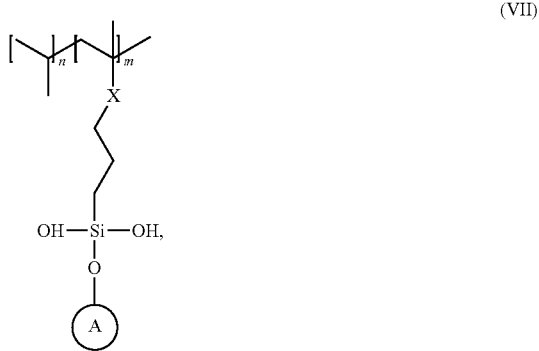

wherein X is methacrylate, "m" is in the range of 0.1 to 20 mole percent, "n" is in the range from 80 to 99.9 mole percent.

Hybrid inorganic-organic micromolecules are copolymerized with polypropylene in the presence of a co-agent, for example, difunctional metallic diacrylate monomers. A co-agent is present during polymerization to stabilize radicals and reduce chain scission of the polypropylene backbone. Free radical processes start with formation of macroradicals along the polymer chains by a so-called hydrogen abstraction mechanism as shown in equation (a). The macroradicals might subsequently follow two competing pathways. They could either initiate the grafting of the monomer or undergo chain scission. The latter depends strongly on the nature of the polymer backbone. In case of PP, the main side reaction is β-scission associated with PP macroradicals, which cause a reduction in the molecular weight of the polymer. In the prior art, styrene was found to be a good comonomer to promote radical grafting and to reduce chain scission of a PP matrix. It was believed to relate to the reactivity towards PP macroradicals; namely, to obtain high grafting yields and to reduce side reactions, it was preferred that the macroradicals react with the grafting monomer rather than undergo side reactions. The so-called 'styrene comonomer concept' was developed in the prior art to improve the grafting yields during free radical modification of polyolefins with maleic anhydride, glycidyl methacrylate and vinyl and acrylic monomers. Cartier H., Hu G-H.: Styrene-assisted melt free radical grafting of glycidyl methacrylate onto polypropylene. Journal of Polymer Science, Part A: Polymer Chemistry, 36, 1053-1063 (1997); Hu G-H., Cartier H.: Styrene-assisted melt free radical grafting of glycidyl methacrylate onto an ethylene and propylene rubber. Journal of Applied Polymer Science, 71, 125-133 (1999); and Cartier H., Hu G-H.: Styrene-assisted free radical grafting of glycidyl methacrylate onto polyethylene in the melt. Journal of Polymer Science Part A: Polymer Chemistry, 36, 2763-2774 (1998). Styrene monomers not advantageous for the purposes of preparing medical devices in that they are considered to provide moderate toxicity and high flammability. In this invention, metal salts having organic functional groups have been selected instead as radical stabilizers. Specifically, diacrylate and/or dimethacryolate monomers offer high temperature stability, easy and safe processability; they are available commercially and used as curing agents for epoxy, rubber, and adhesive systems.

Exemplary co-agents are organo-metal salts. The organo-metal salts may be according to general formula (VI):

wherein "M" is a metal selected from the group consisting of Na, Ca, Mg, Zn, Al and Fe (III). "$X_2$" is an organo-functional group containing at least one double bond, independent from the organo-functional silanes ("X'"). In a preferred embodiment "$X_2$" of the co-reagent is the same as "X" of the organo-functional silane. In a preferred embodiment "$X_2$" is (meth)acrylate, which is defined to include both methacrylates and acrylates.

Exemplary co-agents include but are not limited to difunctional zinc diacrylate or zinc dimethacrylate co-agent according to formulas VIII-A and VIII-B, respectively.

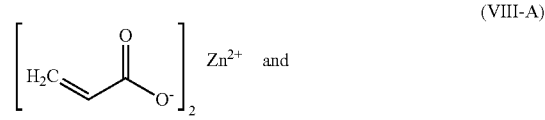

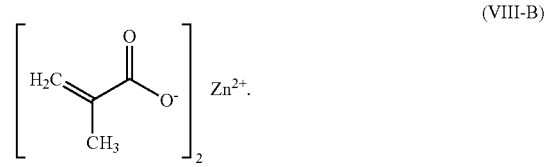

The radical stabilization reaction proceeds according to (d) when, for example, a zinc (meth)acrylate is used.

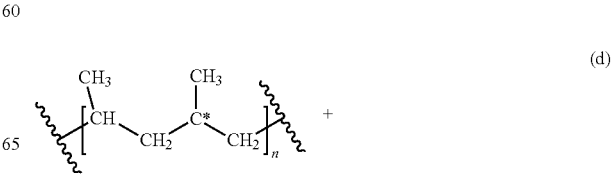

-continued

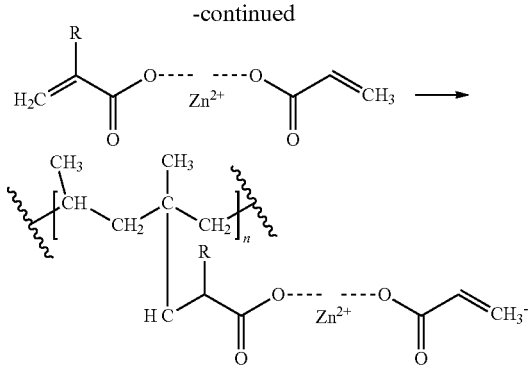

wherein R is H or CH$_3$.

It is understood that there is the potential for grafting on to PP difunctional metallic diacrylate side-chains, according to equation (d-1):

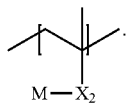 (d-1)

Difunctional zinc diacrylate and zinc dimethacrylate monomers are commercially available product from Sartomer, ictchemicals, Crayvalley and Esstech, Inc. Acrylic and methacrylic salts suitable for use in this process include salts of Na, Ca, Mg, Zn, Al and Fe (III).

In one or more embodiments, the amphiphilic graft copolymer has a melting point in the range of 140 to 180° C.

In one or more embodiments, the amphiphilic graft copolymer has a capillary viscosity in the range of 100 to 300 Pa·s at 180 s$^{-1}$.

In one or more embodiments, the amphiphilic graft copolymer has a weight average molecular weight (Mw) in the range of about 100,000 to about 350,000 g/mol.

In one or more embodiments, the amphiphilic graft copolymer has a dispersity index in the range of 1.5 to 9, or 1.5 to 8, or 1.5-5.

In one or more embodiments, the amphiphilic graft copolymer has a long chain branching frequency in the range of 0.007 to 0.017 per 1000 carbon.

In one or more embodiments, the amphiphilic graft copolymer has a melt flow rate in the range of 15 to 55, or 20 to 40, or 25-35 g/10 minutes in accordance with ASTM 1238-13 method.

In one or more embodiments, polymerization is performed at a reaction temperature in the range of 20° C. to 40° C. In a specific embodiment, the polymerization is performed at a reaction temperature of about 25° C.

In one or more embodiments, the polymerization is performed by solution polymerization. In one or more embodiments, the polymerization is performed by melt processing.

POLYMERIZATION

Solution polymerization may be used for the synthesis, where the starting materials are in a solvent-based solution. Melt processing may also be used, which may include a twin screw extruder above melting temperature of PP. The term "melt processing" is used to mean any process in which polymers, such as the polyolefin, are melted or softened.

Melt processing includes extrusion, pelletization, film blowing or casting, thermoforming, compounding in polymer melt form, fiber spinning, or other melt processes.

Any equipment suitable for a melt processing can be used as long as it provides sufficient mixing and temperature control. For instance, a continuous polymer processing system such as an extruder, a static polymer mixing device such as a Brabender blender, or a semi-continuous polymer processing system, such as a BANBURY mixer, can be used. The term "extruder" includes any machine for polyolefin and TPE extrusion. For instance, the term includes machines that can extrude material in the form of powder or pellets, sheets, fibers, or other desired shapes and/or profiles. Generally, an extruder operates by feeding material through the feed throat (an opening near the rear of the barrel) which comes into contact with one or more screws. The rotating screw(s) forces the polyolefin forward into one or more heated barrels (e.g., there may be one screw per barrel). In many processes, a heating profile can be set for the barrel in which three or more independent proportional-integral-derivative controller (PID)-controlled heater zones can gradually increase the temperature of the barrel from the rear (where the plastic enters) to the front. When a melt extrusion is used, the mixing can take place during the melt extrusion step. The heat produced during the extrusion step provides the energy necessary for the mixing between different components. A temperature at or above the melting temperature of the polymer may be maintained for a time sufficient to mix all the components. For instance, the mixing time may be at least 5 seconds, at least 10 seconds, or at least 15 seconds. Typically, the mixing time is 15-90 seconds.

BLENDS FOR MEDICAL DEVICES

A base polymeric formulation is a material from which a medical device may be made. Preferably, the base polymeric formulations utilized in conjunction with the amphiphilic graft copolymers disclosed herein comprise at least a polymer or co-polymer of ethylene or polyethylene. The base formulation may further include other ingredients, independently selected from one or more of the following: reinforcing and non-reinforcing fillers, plasticizers, antioxidants, stabilizers, processing oil, extender oils, lubricants, antiblocking, antistatic agents, waxes, foaming agents, pigments, flame retardants and other processing aids known in the compounding art. Fillers and extenders which can be utilized include conventional inorganics such as calcium carbonate, clays, silica, talc, titanium dioxide, carbon black, and the like. The processing oils generally are paraffinic, naphthenic or aromatic oils derived from petroleum fractions. The oils are selected from those ordinarily used in conjunction with the specific plastics or rubbers present in the formulation.

An additive is a component added to a formulation which is not reactive within the formulation.

Base polymeric materials with PP-g-XSiOA additive prepared with according to the process of the invention may be formed into useful articles by standard forming methods known in the art, e.g., by blown film extrusion, cast film extrusion, injection or blow molding, pelletizing, foaming, thermoforming, compounding in polymer melt form, or fiber spinning. For example, any technique discussed above in the embodiments describing the melt processes can be used to prepare modified polymer, thereby forming various useful articles, depending on the type of melt processing technique used. For instance, blend may be used in making films, such as blown or cast films. The techniques of blown film extrusion and cast film are known to one skilled in the art in the area of production of thin plastic films. Polymers with PP-g-XSiOA additive may also be used in coextruded films. The formation of coextruded blown films is known to one skilled in the art. The term "coextrusion" refers to the process of extruding two or more materials through a single die with two or more orifices arranged such that the extrudates merged together into a laminar structure, for instance, before chilling or quenching.

TABLE I

Exemplary Formulations (with the proviso that the ingredients total 100%). To the exemplary formulations, antimicrobial agents may be added in amounts of 0.02 wt. % to 3 wt. % and all values and subranges there between of the total formulation.

| Blend Ingredient | A by weight | B by weight | C by weight |
|---|---|---|---|
| Base Polymeric Formulation | 80-99.99% | 80-99.99% | 80-99.99% |
| Polypropylene | 50-100% | 0-50% | 0-50% |
| Polyethylene | 0-50% | 50-100% | 0-50% |
| Polypropylene-containing Thermoplastic elastomer (TPE) | 0-50% | 0-50% | 50-100% |
| Optional further ingredients | 0-10% | 0-10% | 0-10% |
| PP-g-XSiOA additive | 0.01-20% | 0.01-20% | 0.01-20% |

In one or more embodiments, including Exemplary Formulations A, B, and C, the PP-g-XSiOA additive may be present in amounts of about 0.01 to about 10.0% by weight; about 0.1 to about 5.0% by weight; about 0.2 to about 2.0% by weight; about 0.25 to about 0.75% by weight; or about 0.5 weight %.

Polypropylene may be any commercially-available material produced by Ziegler-Natta, Metallocene, or any other olefin polymerization catalyst. Propylene polymers may be homopolymers or copolymers (random or impact). In applications where polypropylene (PP) and polyethylene blends are used, random and impact PP copolymers are preferred; improved compatibility of propylene and ethylene polymers comes from C2 content in the random PP grades. Higher compatibility results in improved physical and mechanical properties for the resulting articles (such as improved tear, dart impact, or puncture resistance in films) as compared with the homopolymer PP resin. The propylene polymers are preferably isotactic or syndiotactic, more preferably isotactic. The preferably melt flow rate of the propylene polymers is in the 0.5-150 g/10 minutes range based on the requirements of the manufacturing process and end applications (230° C./2.16 kg, ASTM D1238-13).

Suitable linear low density polyethylene (LLDPE) for use in the process of the invention include copolymers of ethylene and α-olefins. Alpha-olefins include 1-butene, 1-hexene, and 1-octene, the like, and mixtures thereof. The density of LLDPE is preferably within the range of about 0.865 to about 0.925 g/cm$^3$ (ASTM D792-13) and a melt mass flow rate of less than 0.5 g/10 min to greater than 20 g/10 min based on the requirements of the manufacturing process and end application (190° C./2.16 kg, ASTM D1238-13). LLDPE is commercially available, for instance Dowlex™ 2045.01 G LLDPE from Dow Chemical Company. Suitable LLDPE can be produced by a Ziegler-Natta, single-site, or any other olefin polymerization catalysts.

Suitable polyethylene-polypropylene co-polymers may include—reactor grade or melt blended mixtures of the polypropylene and polyethylene polyolefins with or without polyolefin elastomers (final formulation containing from but not limited to about 10 wt.-% up to about 80 wt.-% ethylene and/or propylene monomeric units). The term "blend" or "polymer blend" generally refers to a mixture of two or more components. Such a blend may or may not be miscible, and may or may not be phase separated.

Suitable polyolefins include those prepared from linear or branched olefins having 2 to 20 carbon atoms, 2 to 16 carbon atoms, or 2 to 12 carbon atoms. Typically, the olefin used to prepare the polyolefin is α-olefin. Exemplary linear or branched α-olefins includes, but are not limited to, ethylene, propylene, 1-butene, 2-butene, 1-pentene, 3-methyl-1-butene, 4-methyl-1-pentene, 3-methyl-1-pentene, 1-hexene, 3,5,5-trimethyl-1-hexene, 4,6-dimethyl-1-heptene, 1-octene, 1-decene, 1-undecene, 1-dodecene, 1-tetradecene, 1-hexadecene, 1-octadecene, and 1-eicocene. These olefins may contain one or more heteroatoms such as an oxygen, nitrogen, or silicon. The term "polyolefin" generally embraces a homopolymer prepared from a single type of olefin monomer as well as a copolymer prepared from two or more olefin monomers. A specific polyolefin referred to herein shall mean polymers comprising greater than 50% by weight of units derived from that specific olefin monomer, including homopolymers of that specific olefin or copolymers containing units derived from that specific olefin monomer and one or more other types of olefin comonomers. The polyolefin used herein can be a copolymer wherein the comonomer(s) is/are randomly distributed along the polymer chain, a periodic copolymer, an alternating copolymer, or a block copolymer comprising two or more homopolymer blocks linked by covalent bonds. Typical polyolefins include polyethylene, polypropylene, a copolymer of polyethylene and polypropylene, and a polymer blend containing polyethylene, polypropylene, and/or a copolymer of polyethylene and polypropylene. Polyolefin can also be an ethylene rich impact copolymer (may contain ethylene comonomer at the amount of at least 10 wt.-%; and up to 40 wt.-%), i.e., a heterophasic polyolefin copolymer where one polyolefin is the continuous phase and an elastomeric phase is uniformly dispersed therein. This would include, for instance, a heterophasic polypropylene copolymer where polypropylene is the continuous phase and an elastomeric phase is uniformly dispersed therein. The impact copolymer results from an in-reactor process rather than physical blending. The polyolefins mentioned above can be made by conventional Ziegler/Natta catalyst-systems or by single-site catalyst-systems.

Suitable polyolefin elastomers for use in the process of the invention include ethylene-propylene rubber (EPR), ethylene-propylene-diene monomer rubber (EPDM), the like, and mixtures thereof. As used herein, the term "elastomer" refers to products having rubber-like properties and little or no crystallinity. Preferably, the polyolefin elastomers contain from about 10 wt.-% up to about 80 wt.-% ethylene monomeric units. Illustrative polyolefin elastomers which are commercially available include Lanxess Corporation's BUNA EP T 2070 (22 Mooney ML (1+4) 125° C., 68% ethylene, and 32% propylene); BUNA EP T 2370 (16 Mooney, 3% ethylidene norbornene, 72% ethylene, and 25% propylene); BUNA EP T 2460 (21 Mooney, 4% ethylidene norbornene, 62% ethylene, and 34% propylene); ExxonMobil Chemical's VISTALON 707 (72% ethylene, 28% propylene, and 22.5 Mooney); VISTALON 722 (72% ethylene, 28% propylene, and 16 Mooney); and VISTALON 828 (60% ethylene, 40% propylene, and 51 Mooney). Suitable EP elastomers available from commercial sources also include ExxonMobil Chemical's VISTAMAXX series of elastomers, particularly VISTAMAXX grades 6100, 1100, and 3000. These materials are ethylene-propylene elastomers of 16, 15, and 11 wt.-% ethylene content, respectively, and a Tg of about −20 to −30° C. VISTAMAXX 6100, 1100, and 3000, respectively, have a melt flow rate of 3, 4, and 7 g/10 minutes at 230° C.; a density of 0.858, 0.862, and 0.871 g/cm$^3$; and a 200 g Vicat softening point of 48, 47, and 64° C. Other suitable elastomers include Dow Chemical's VERSIFY propylene-ethylene copolymers, particularly grades DP3200.01, DP3300.01, and DP3400.01, which have nominal ethylene contents of 9, 12 and 15 wt.-%, respectively, and corresponding nominal propylene contents of 91, 88, and 85 wt.-%, respectively. These grades have a melt flow rate of 8 g/10 minutes at 230° C.; a density of 0.876, 0.866, and 0.858 g/cm$^3$, respectively; a Vicat softening point of 60, 29, and <20° C., respectively; and a Tg of −25, −28, and −31° C., respectively.

Preferably, the polyolefin elastomers contain from but not limited to about 10 wt.-% up to about 80 wt.-% ethylene monomeric units. The term "thermoplastic elastomer" (TPE) in general defines blends of polyolefins and rubbers in which blends of the rubber phase is not cured, i.e., so called thermoplastic olefins (TPO), blends of polyolefins and rubbers in which blends of the rubber phase has been partially or fully cured by a vulcanization process to form thermoplastic vulcanizates (TPV), or unvulcanized block-copolymers or blends thereof. Non-polar thermoplastic elastomer may made from a thermoplastic polyolefin homopolymer or copolymer, and an olefinic rubber which is fully crosslinked, partially crosslinked or not crosslinked, and optionally commonly used additives; as well as a block-copolymer of styrene/conjugated diene/styrene and/or its fully or partially hydrogenated derivative.

Polyolefins suitable for use in TPE composition include thermoplastic, crystalline polyolefin homopolymers and copolymers. They are desirably prepared from monoolefin monomers having but not limited to 2 to 7 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth)acrylates and/or vinyl acetates. The polyolefins which can be used in TPE formulations can be a high, low, linear-low, very low-density polyethylenes and copolymers of ethylene with (meth)acrylates and/or vinyl acetates. Polyolefins can be made by conventional Ziegler/Natta catalyst-systems or by single-site catalyst-systems, or other polyolefin catalyst technology in combination with various process technologies and solutions.

Suitable olefinic rubbers of the monoolefin copolymer rubbers comprise non-polar, rubbery copolymers of two or more α-monoolefins, preferably copolymerized with at least one polyene, usually a diene. Saturated monoolefin copolymer rubber, for example ethylene-propylene copolymer rubber (EPM) can be used. However, unsaturated monoolefin rubber such as EPDM rubber is more suitable. EPDM is a terpolymer of ethylene, propylene and a non-conjugated diene. Satisfactory non-conjugated dienes include 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; dicyclopentadiene (DCPD) and vinyl norbornene (VNB). Butyl rubbers are also used in TPE formulation. The term "butyl rubber" includes copolymers of an isoolefin and a conjugated monoolefin, terpolymers of an isoolefin with or without a conjugated monoolefin, divinyl aromatic monomers and the halogenated derivatives of such copolymers and terpolymers. Another suitable copolymer within the olefinic rubber is a copolymer of a $C_{4-7}$ isomonoolefin, and a para-alkylstyrene. A further olefinic rubber used in TPE is natural rubber. The main constituent of natural rubber is the linear polymer cis-1,4-polyisoprene. Furthermore polybutadiene rubber and styrene-butadiene-copolymer rubbers can also be used. Blends of any of the above olefinic rubbers can be employed, rather than a single olefinic rubber. Further suitable rubbers are nitrite rubbers. Examples of the nitrile group-containing rubber include a copolymer rubber comprising an ethylenically unsaturated nitrile compound and a conjugated diene. Further, the copolymer rubber may be one in which the conjugated diene units of the copolymer rubber are hydrogenated. Specific examples of the ethylenically unsaturated nitrile compound include acrylonitrile, α-chloroacrylonitrile, α-fluoroacrylonitrile and methacrylonitrile. Among them, acrylonitrile is particularly preferable. Other suitable rubbers are based on polychlorinated butadienes such as polychloroprene rubber. These rubbers are commercially available under the trade names Neoprene® and Bayprene®.

A commercially available thermoplastic elastomer (TPE) for use herein may be one formulated without plasticizers having a nominal density of 0.888 g/cm$^3$ (ASTM D792-13) and a nominal composition of: 33.0 mol % propylene, 24.8 mol % ethylene, and 42.2 mol % butylene.

APPLICATIONS

The amphiphilic graft copolymers in the form of functionalized-PP materials may advantageously be used as modifier in a base polymer formulation, e.g., TPE or polyolefins. The modified base polymer formulations have improved properties with respect to, for example, antimicrobial properties. The amphiphilic graft copolymers may be co-blended with base formulations to enhance properties of medical devices that are formed by injection molding or by extrusion.

The amphiphilic graft copolymers may be blended with polyolefins or TPE for forming medical devices. Suitable blending temperature during melt mixing should be sufficient to melt or to soften the component of the composition which has the highest melting or softening point. The temperature typically ranges from 60 to 300° C., for instance, from 100 to 280° C., from 90 to 150° C. One skilled in the art understands that a polyolefin or TPE mixtures thereof typically melts or softs over a temperature range rather than sharply at one temperature. Thus, it may be sufficient that the polyolefin be in a partially molten state. The melting or softening temperature ranges can be approximated from the differential scanning calorimeter (DSC) curve of the polyolefin or mixtures thereof.

Modified PP and PPBMs can be beneficially used (as a single component and as an additive) in making parts of the medical devices including, but not limited to balloon catheters, tubing for feeding, drainage, and use with peristaltic pumps, compression bars, electrosurgical hand pieces, infusion sleeves and test chambers, introducer tips and flexible sheaths, ear plugs and hearing aids, shunts and septums and a variety of seals, stoppers, valves, and clips; as well as for applications such as IV tubing, catheter extension set tubing and catheter tubing. For all of these applications there is a drive further enhance, and differentiate, the performance attributes of these devices and components. There is an additional desire from GPOs, NGOs, and regulatory to remove DEHP and other phthalate-based plasticizers from the formulation as well as to eliminate the use of PVC entirely.

Many TPE formulations use some type of plasticizer in their formulation and most IV tubing and extension sets are comprised of plasticized PVC. Additionally, for the stopper application there is a desire to move from the conventional thermal-set rubbers to an injection moldable thermoplastic elastomer which can also be reprocessed, resulting in processing efficiencies and potential cost savings.

Moreover, modification technology has potential to improve unmet PP based materials properties needs, such as—antimicrobial properties.

ANTIMICROBIAL PROPERTIES

Medical devices herein have enhanced antimicrobial properties when formed from a base polymer combined with an amphiphilic graft copolymer (polypropylene (PP) via hybrid organic silane and difunctional metallic diacrylate chemistry) and one or more antimicrobial agents. The PP-based amphiphilic graft copolymers are more hydrophilic than PP alone by incorporating functional groups based on hybrid organic silane micromolecules in combination with the difunctional metallic diacrylate monomers.

The presence of organic hybrid micromolecules in the polymer (e.g., polypropylene) increases affinity of the polymer matrix with antimicrobial agents, achieves antimicrobial properties at low concentration levels and improves antimicrobial agent release rate. This phenomena can be explained by unique nature of amphiphilic copolymers which are acting as compatibilizer agents between polymers and inorganic additives and thus achieving good antimicrobial performance of polymer at low concentration level of the antimicrobial additives via homogeneous dispersion and improved interactions (adhesion) with the polymer matrix.

As described above antimicrobial agents may be selected from the group consisting of: berberine chloride, berberine chloride hydrate, octinedine dihydrochloride, 4-chlorophenyl methyl sulfone, climbazole, piroctone olamine, silver sulfadiazine, copper particles, silver particles, and combinations thereof.

Relative to medical devices made from polymers without the presence of a copolymer additive comprising a copolymer having a polypropylene backbone and hybrid micromolecule side-chains based on organo-functional silanes, the inventive blends of polymers including an additive comprising a copolymer having a polypropylene backbone and hybrid micromolecule side-chains based on organo-functional silanes show lower bacteria growth as constant antimicrobial agent concentration. Similarly, the presence of the copolymer additive means that less antimicrobial agent is needed for effective antimicrobial properties as compared to devices that do not have the copolymer additive.

EMBODIMENTS

Various embodiments are listed below. It will be understood that the embodiments listed below may be combined with all aspects and other embodiments in accordance with the scope of the invention.

Embodiment 1

A medical device comprises: a polymeric body comprising: a base polymeric formulation comprising at least a polymer or co-polymer of propylene; and an additive comprising a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; the PP-g-XSiOA being in a blend with the base polymeric formulation in an amount in the range of about 0.01 to about 20.0% by weight of the blend; and an antimicrobial agent.

Embodiment 2

The medical device of embodiment 1, wherein the antimicrobial agent comprises: berberine chloride, berberine chloride hydrate, octinedine dihydrochloride, 4-chlorophenyl methyl sulfone, climbazole, piroctone olamine, silver sulfadiazine, copper particles, silver particles, or combinations thereof.

Embodiment 3

The medical device of embodiment 2, wherein the antimicrobial agent may be present in an amount in the range of 0.02 to 3% by weight of the blend of additive and base polymeric formulation.

Embodiment 4

The medical device of one of embodiments 1 to 3, wherein the PP-g-XSiOA is an amphiphilic copolymer comprising polypropylene and an inorganic-organic hybrid micromolecule, which is according to Formula (I):

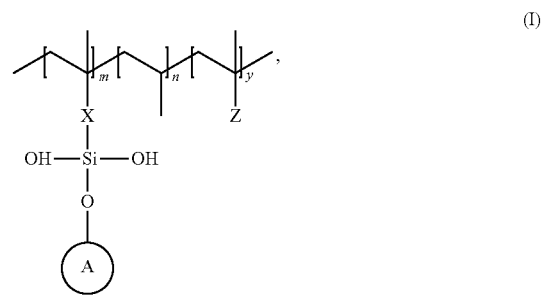

wherein X is an organic or an organo-functional group containing 1 to 6 carbons; A is a metal, an inorganic oxide, an inorganic hydroxide, or any other inorganic material; and n is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X$_2$; XSiOR; or XSiOH, wherein "M-X$_2$" is an organo-metal salt and "OR" is an alkoxy group having 1 to 4 carbons.

Embodiment 5

The medical device of one of embodiments 1 to 4, wherein the base polymeric formulation comprises polypropylene, a polyethylene-polypropylene co-polymer, a polypropylene-containing thermoplastic elastomer (TPE), or combinations thereof.

Embodiment 6

The medical device of one of embodiments 1 to 5, wherein X is derived from a compound selected from the group consisting of epoxy, amino, acrylate, methacryloxy, and vinyl; and A is selected from the group consisting of:

silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

Embodiment 7

The medical device of one of embodiments 1 to 6 having a melting point in the range of 140 to 180° C.

Embodiment 8

The medical device of one of embodiments 1 to 7 having a capillary viscosity in the range of 100 to 300 Pa·s at 180 s$^{-1}$.

Embodiment 9

The medical device of one of embodiments 1 to 8 having a weight average molecular weight (Mw) in the range of about 100,000 to about 350,000 g/mol.

Embodiment 10

The medical device of one of embodiments 1 to 9 having a dispersity index in the range of 1.5 to 9.

Embodiment 11

The a medical device of one of embodiments 1 to 10 having a long chain branching frequency in the range of 0.007 to 0.017 per 1000 carbon.

Embodiment 12

The medical device of one of embodiments 1 to 11 having a melt flow rate in the range of 15 to 55 g/10 minutes.

Embodiment 13

The medical device of one of embodiments 1 to 12 in the form of tubing, barrel, rod, or any other geometric shape.

Embodiment 14

A method of making a medical device comprises obtaining a copolymer having a polypropylene backbone and hybrid micromolecule side-chains based on organo-functional silanes (PP-g-XSiOA), where "X" is an organic group or an organo-functional group; and "A" is a metal, an inorganic oxide, an inorganic hydroxide, or any other inorganic material; combining the PP-g-XSiOA with a base polymeric formulation comprising at least a polymer or co-polymer of propylene to form a blend, the PP-g-XSiOA being present in the blend in an amount in the range of about 0.01 to about 20.0% by weight of the blend; adding an antimicrobial agent to the blend to form a mixture; and forming a polymeric body from the mixture.

Embodiment 15

The method of embodiment 14 wherein the antimicrobial agent comprises: berberine chloride, berberine chloride hydrate, octinedine dihydrochloride, 4-chlorophenyl methyl sulfone, climbazole, piroctone olamine, silver sulfadiazine, copper particles, silver particles, or combinations thereof.

Embodiment 16

The method of one of embodiments 14 to 15, wherein the base polymeric formulation comprises polypropylene, a polyethylene-polypropylene co-polymer, a polypropylene-containing thermoplastic elastomer (TPE), or combinations thereof.

Embodiment 17

The method of one of embodiments 14 to 16, wherein the PP-g-XSiOA is according to Formula (I):

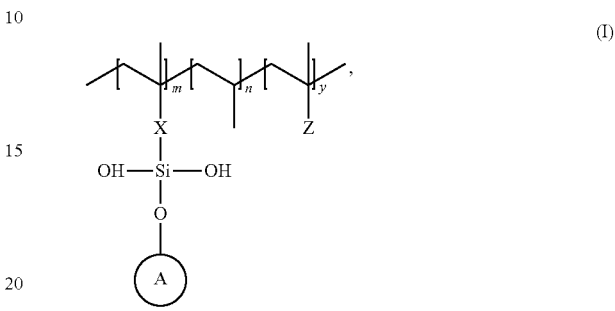

wherein X is an organic group or an organo-functional group; A is a metal, an inorganic oxide, an inorganic hydroxide, or any other inorganic material; and "n" is in the range of about 78 to 99.9 mole percent; m is in the range of about 0.1 to 20 mole percent; the molar value of "y" is in the range of about 0 to 2.0 mole percent; and "Z", when y is greater than 0, comprises: M-X$_2$; XSiOR; or XSiOH, wherein "M-X$_2$" is an organo-metal salt and "OR" is an alkoxy group having 1 to 4 carbons.

Embodiment 18

The method of one of embodiments 14 to 17, wherein X of the PP-g-XSiOA is derived from a compound selected from the group consisting of epoxy, amino, acrylate, methacryloxy, and vinyl; and A is selected from the group consisting of: silicon, (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

Embodiment 19

The method of one of embodiments 14 to 18, wherein the medical device is in the form of tubing, barrel, rod, or any other geometric shape.

EXAMPLES

The following materials were used for synthesis of amphiphilic graft copolymers PP-g-XSiOA and comparative polymers.

Organic silane: 3-(Trimethoxysilyl)propyl methacrylate (synonym: [3-(Methacryloyloxy)propyl] trimethoxysilane) obtained from Sigma-Aldrich.

Silica (synonyms: silica, silicic anhydride, silicon dioxide amorphous, silicon dioxide) and aluminum oxyhydroxide (AlO(OH)) having average particle size 0.1-0.5 µm (aggregate), obtained both from Sigma-Aldrich.

LUPEROX 101: (synonym: 2,5-Bis(tert-butylperoxy)-2,5-dimethylhexane; 2,5-Bis(tert-butylperoxy)-2,5-dimethylhexane) obtained from Sigma-Aldrich.

Polypropylene (PP): commercial grade PP homopolymer (made by a Ziegler-Natta catalyst); melt flow of the PP was 3.6 g/10 minutes (measured at 230° C. and 2.16 kg weight—ASTM method D1238-13.

Co-agent difunctional zinc dimethacrylate: (synonyms: zinc methacrylate and methacrylic acid zinc salt) obtained from Sigma-Aldrich.

Example 1

Polymers were synthesized according to the formulations of Table 1 in weight % with respect to the polypropylene (PP) content. Formulations 5-7 were inventive as modifications of base polypropylene.

TABLE 1

| Component wt.-% | PP | Peroxide | Monomer 1[a] | Monomer 2[b] | Co-agent |
|---|---|---|---|---|---|
| Formulation 1 Comparative | 100 | 0 | 0 | 0 | 0 |
| Formulation 2 Comparative | 100 | 0.25 | 0 | 0 | 0 |
| Formulation 3 Comparative | 100 | 0.25 | 1 | 0 | 0 |
| Formulation 4 Comparative | 100 | 0.25 | 0 | 0 | 1.0 |
| Formulation 5 | 100 | 0.25 | 0 | 0.5 | 0.2 |

TABLE 1-continued

| Component wt.-% | PP | Peroxide | Monomer 1[a] | Monomer 2[b] | Co-agent |
|---|---|---|---|---|---|
| Formulation 6 | 100 | 0.25 | 0 | 1 | 0.2 |
| Formulation 7 | 100 | 0.25 | 0 | 1.5 | 0.2 |

[a]Neat 3-(Trimethoxysilyl)propyl methacrylate
[b]Hybrid micromolecule synthesized based on silica + 3-(Trimethoxysilyl)propyl methacrylate Synthesis experiments were performed on a ZSK 30 mm twin screw extruder. To avoid degradation/oxidation experiments were done under $N_2$ blanket Before extrusion experiments, reaction components such as PP, monomers, co-agents and peroxide were blended together using Henschel automated mixing equipment. Blended mixture of the reaction components was fed to the extruder from the main feeder. Table 2 summarizes conditions of the extrusion process.

TABLE 2

| Condition | Torque % | Extruder RPM | Melt Temperature (° F.) |
|---|---|---|---|
| Formulation 1 Comparative | 60 | 266 | 478 |
| Formulation 2 Comparative | 37 | 262 | 449 |
| Formulation 3 Comparative | 36 | 262 | 414 |
| Formulation 4 Comparative | 35 | 261 | 422 |
| Formulation 5 | 38 | 260 | 421 |
| Formulation 6 | 31 | 260 | 422 |
| Formulation 7 | 31 | 258 | 460 |

Example 2

Blends of PP and amphiphilic graft copolymers and comparative formulations according to Table 1 were prepared at 220° C. using a Rheomex OS 16 mm twin screw extruder from Thermo Fisher Scientific. The compositions are provided in Table 3.

TABLE 3

| | | | Component wt.-% | | | | | |
|---|---|---|---|---|---|---|---|---|
| Group # | Name | PP | Formulation 6 | Berberine chloride | Octinedine dihydro- chloride | sulfadiazine | Copper | Silver |
| 1* | Cont-PP | 100 | 0 | 0 | 0 | 0 | 0 | 0 |
| | Cont-PP-M10 | 90 | 10 | 0 | 0 | 0 | 0 | 0 |
| 2* | Cont-PP-AD1-1 | 100 | 0 | 1 | 0 | 0 | 0 | 0 |
| | Cont-PP-AD2-1 | 100 | 0 | 0 | 1 | 0 | 0 | 0 |
| | Cont-PP-AD3-1 | 100 | 0 | 0 | 0 | 1 | 0 | 0 |
| | Cont-PP-AD4-1 | 100 | 0 | 0 | 0 | 0 | 1 | 0 |
| | Cont-PP-AD5-1 | 100 | 0 | 0 | 0 | 0 | 0 | 1 |
| 3* | Cont-PP-AD1-3 | 100 | 0 | 3 | 0 | 0 | 0 | 0 |
| | Cont-PP-AD2-3 | 100 | 0 | 0 | 3 | 0 | 0 | 0 |
| | Cont-PP-AD5-3 | 100 | 0 | 0 | 0 | 0 | 0 | 3 |
| 4 | PP-AD1-1 | 90 | 10 | 1 | 0 | 0 | 0 | 0 |
| | PP-AD2-1 | 90 | 10 | 0 | 1 | 0 | 0 | 0 |
| | PP-AD3-1 | 90 | 10 | 0 | 0 | 1 | 0 | 0 |
| | PP-AD4-1 | 90 | 10 | 0 | 0 | 0 | 1 | 0 |
| | PP-AD5-1 | 90 | 10 | 0 | 0 | 0 | 0 | 1 |

*Groups 1-3 are controls. Group 1 does not contain antimicrobial agent. Groups 2-3 do not contain an amphiphilic graft copolymer.

Specimens using compositions of Table 3 were prepared by compression molding at 200° C.

Example 3

Testing

Differential Scanning calorimetry (DSC). Two heating steps and one cooling step were performed for each sample under −20 to 200° C. temperature range, using 10° C./min heating rate. Collected DSC thermograms were used to calculate melting, crystallization temperatures and degree of crystallinity.

Figure 2:
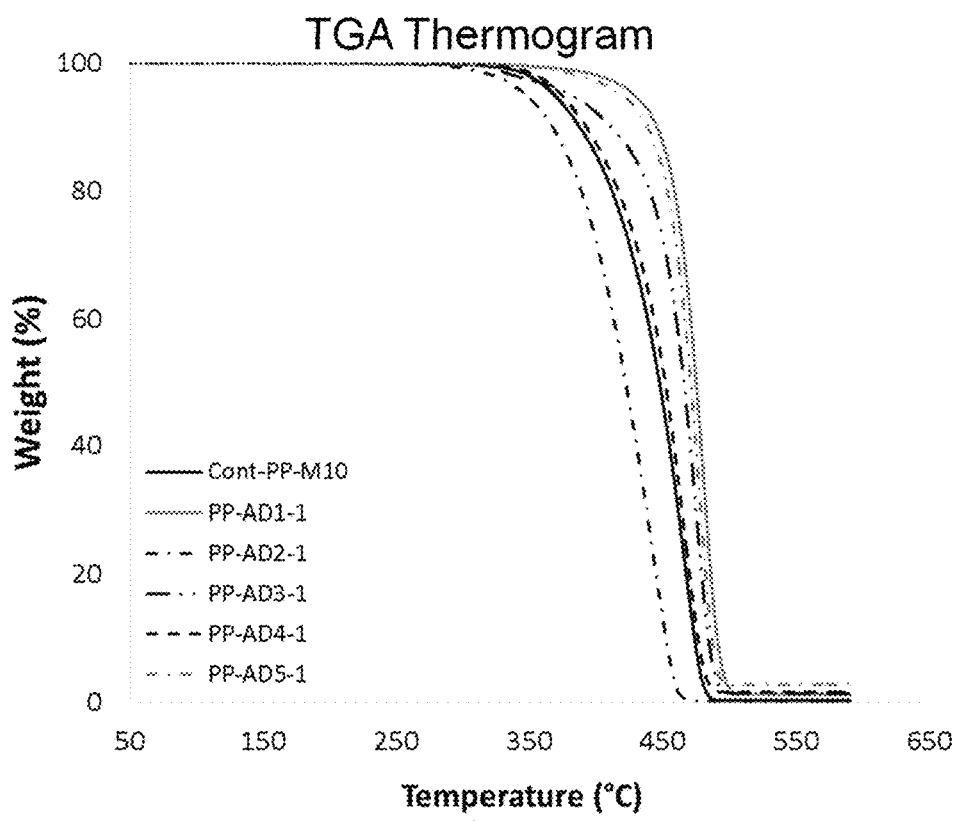
FIG. 2 provides a thermogram from thermogravimetric analysis (TGA). TGA curve of weight % versus temperature (° C.) for control composition Group 1 "Cont-PP-M10 and for the inventive compositions of Group 4 of Table 3.

Table 4 shows DSC data including crystallization temperature ($T_c$), % crystallinity, melting point ($T_m$), % crystallinity after second step. FIG. 1 provides a thermogram of weight % versus temperature (° C.) for control compositions: Group 1 "Cont-PP" and Group 2 of Table 3. FIG. 2 provides a thermogram of weight % versus temperature (° C.) for control composition Group 1 "Cont-PP-M10 and for the inventive compositions of Group 4 of Table 3.

Compare to comparative samples or to Cont-PP-M10 samples without antimicrobial agents, modified PP containing samples with the same amount of agent content showed thermal stability increate at 450° C. Compared to comparative samples without modified PP such as for example Cont-PP-AD1-1, % of residual is ~24% higher than for PP-AD1-1 samples which contains the same type and amount of the agent in addition to modified PP. There is the same observation for all other agents, with the only exception being PP-AD2-1 formulation.

TABLE 4

| Group # | Name/Description | $T_c$ (° C.) | Crystallinity %[a] | $T_m$ (° C.) | Crystallinity %[a] |
|---|---|---|---|---|---|
| 1* | Cont-PP | 119.8 | 44.8 | 162.7 | 41.4 |
|  | Cont-PP-M10 | 117.6 | 48.5 | 162.7 | 43.1 |
| 2* | Cont-PP-AD1-1 | 119.9 | 46.7 | 162.6 | 41.9 |
|  | Cont-PP-AD2-1 | 116.9 | 46.1 | 161.6 | 40.7 |
|  | Cont-PP-AD3-1 | 116.9 | 45.1 | 161.4 | 41.7 |
|  | Cont-PP-AD4-1 | 116.2 | 45.2 | 161.6 | 41.1 |
|  | Cont-PP-AD5-1 | 118.0 | 45.8 | 162.0 | 41.8 |
| 4 | PP-AD1-1 | 124.2 | 47.6 | 163.7 | 43.7 |
|  | PP-AD2-1 | 117.4 | 44.1 | 163.2 | 39.4 |
|  | PP-AD3-1 | 123.4 | 46.6 | 164.1 | 42.3 |
|  | PP-AD4-1 | 115.9 | 45.0 | 161.9 | 40.8 |
|  | PP-AD5-1 | 122.8 | 46.2 | 162.9 | 43.7 |

[a]Degree of crystallinity (%) = ($\Delta H_m / \Delta H_{mo}$) × 100 $\Delta Hm_0$ is a reference value and represents the heat of melting of "100% crystalline" polymer. $\Delta Hm_0$ of 100% crystalline PP is 207.1 (J/g)

Antimicrobial agent content (type and amount) does not effect on the degree of polymer crystallinity and melting point. % of crystallinity stays almost the same and across all samples (including comparative) we see approximately 1-2% change.

Antimicrobial agent content (type and amount) impacts crystallization (Tc) temperature of the polymer when added 10% modified PP formulation 6. For modified samples, there was about a 5-7° C. temperature shift, while for comparative samples with the same type of antimicrobial agent content, Tc change was 2-3° C.

With exception of PP-AD4-1 sample, Tc values of modified PP samples increased after addition of the antimicrobial agents. Tc of modified PP samples with antimicrobial agents is higher than Cont-PP-M10 or comparative samples with the same type of agents. Tc increase can be explained by the fact that modified PP improved additive dispersion and homogenously dispersed antimicrobial agents are acting as nucleating seeds which accelerate crystallization and increases Tc.

Thermogravimetric analysis (TGA). TGA measurements were performed in 30 to 550° C. temperature range using 10° C./min heating rate. Table 5 provides residue (wt. %) data at various temperatures.

TABLE 5

| Group # | Name/Description | Residue (wt. %) at |  |  |  |  |
|---|---|---|---|---|---|---|
|  |  | 150° C. | 250° C. | 350° C. | 450° C. | 550° C. |
| 1* | Cont-PP | 100 | 100 | 98.7 | 53.9 | 0.3 |
|  | Cont-PP-M10 | 100 | 100 | 98.2 | 48.7 | 0.2 |
| 2* | Cont-PP-AD1-1 | 100 | 100 | 99.4 | 49.8 | 0.8 |
|  | Cont-PP-AD2-1 | 100 | 100 | 98.0 | 65.3 | 0.2 |
|  | Cont-PP-AD3-1 | 100 | 100 | 96.7 | 52.6 | 1.2 |
|  | Cont-PP-AD4-1 | 100 | 100 | 99.1 | 54.5 | 1.6 |
|  | Cont-PP-AD5-1 | 100 | 100 | 99.3 | 67.0 | 1.5 |
| 4 | PP-AD1-1 | 100 | 100 | 99.5 | 73.8 | 1.2 |
|  | PP-AD2-1 | 100 | 100 | 95.5 | 29.6 | 0.1 |
|  | PP-AD3-1 | 100 | 100 | 97.3 | 70.2 | 1.3 |
|  | PP-AD4-1 | 100 | 100 | 99.2 | 69.6 | 1.6 |
|  | PP-AD5-1 | 100 | 100 | 99.2 | 72.8 | 2.5 |

Antimicrobial agent and modified PP content in the formulation has significant effect on the thermal stability behavior of samples. Especially, thermal stability of the polymer above 350-400° C.

TGA and DSC observations and differences between comparative and inventive samples once again indicates that modification technology effects agent/polymer matrix interactions which effects overall properties of the polymers including antimicrobial behaviors.

Thermal stability increase can be explained by the fact that modified PP improved additive dispersion and interactions between polymer and additive surfaces.

Mechanical Properties—Flexure. Flexure properties were measured in accordance with ASTM D-790:2010 using an Instron 5566 materials testing system. Tables 6A and 6B provide various flexure properties.

TABLE 6A

| Sample Name | Elastic Modulus (psi) | % RSD | Offset Yield Stress (psi) | % RSD | 1% Secant Modulus (psi) | % RSD |
|---|---|---|---|---|---|---|
| Cont-PP | 134 128 | 1.5 | 3124 | 2.2 | 133 965 | 1.9 |
| Cont-PP-M10 | 132 770 | 0.7 | 2925 | 1.4 | 132 588 | 0.7 |
| Cont-PP-AD1-1 | 132 125 | 1.2 | 3130 | 1.0 | 132 416 | 1.2 |
| Cont-PP-AD2-1 | 130 002 | 0.5 | 2719 | 0.5 | 129 610 | 0.5 |
| Cont-PP-AD3-1 | 131 621 | 1.1 | 3258 | 2.2 | 132 435 | 1.4 |
| Cont-PP-AD4-1 | 133 994 | 2.6 | 3259 | 3.6 | 133 540 | 1.7 |
| Cont-PP-AD5-1 | 137 497 | 0.9 | 3332 | 1.3 | 137 652 | 0.9 |
| PP-AD1-1 | 144 843 | 1.8 | 3747 | 1.1 | 144 302 | 1.5 |
| PP-AD2-1 | 142 229 | 1.4 | 3465 | 3.5 | 144 390 | 1.2 |
| PP-AD3-1 | 142 518 | 3.1 | 3561 | 6.1 | 143 402 | 1.8 |
| PP-AD4-1 | 143 894 | 1.7 | 3960 | 1.2 | 146 780 | 1.4 |
| PP-AD5-1 | 151 094 | 0.9 | 4175 | 1.5 | 151 397 | 1.3 |

TABLE 6B

| Sample Name | Strain at Offset Yield (in/in) | Flexural Strength at Yield (psi) | Flexural Strain at Yield (in/in) | Flexural Strength at 5% (psi) | % RSD |
|---|---|---|---|---|---|
| Cont-PP | 0.025 | 4788 | 0.08 | 4440 | 0.3 |
| Cont-PP-M10 | 0.02 | 4882 | 0.08 | 4449 | 0.6 |

TABLE 6B-continued

| Sample Name | Strain at Offset Yield (in/in) | Flexural Strength at (psi) | Flexural Strain at Yield (in/in) | Flexural Strength at 5% (psi) | % RSD |
|---|---|---|---|---|---|
| Cont-PP-AD1-1 | 0.02 | 4563 | 0.08 | 4449 | 0.5 |
| Cont-PP-AD2-1 | 0.02 | 4558 | 0.07 | 4172 | 0.4 |
| Cont-PP-AD3-1 | 0.03 | 4455 | 0.07 | 4138 | 1.2 |
| Cont-PP-AD4-1 | 0.03 | 4624 | 0.08 | 4244 | 0.3 |
| Cont-PP-AD5-1 | 0.02 | 4821 | 0.07 | 4420 | 1.0 |
| PP-AD1-1 | 0.02 | 5586 | 0.08 | 5236 | 1.1 |
| PP-AD2-1 | 0.02 | 5489 | 0.07 | 5139 | 1.3 |
| PP-AD3-1 | 0.02 | 5557 | 0.07 | 5205 | 0.3 |
| PP-AD4-1 | 0.02 | 4103 | 0.07 | 5725 | 0.9 |
| PP-AD5-1 | 0.02 | 5148 | 0.07 | 4780 | 0.7 |

Mechanical Properties—Tensile. Tensile properties were measured in accordance with ASTM D-638:2010 using an Instron 5566 materials testing system. Tables 7A and 7B provide various tensile properties.

TABLE 7A

| Sample Name | Elastic Modulus (psi) | % RSD | Offset Yield Stress (psi) | % RSD | Strain at Offset Yield (in/in) | Strain at Yield (in/in) |
|---|---|---|---|---|---|---|
| Cont-PP | 184 290 | 3.0 | 2391 | 1.1 | 0.01 | 0.11 |
| Cont-PP-M10 | 184 534 | 2.4 | 2166 | 3.1 | 0.01 | 0.12 |
| Cont-PP-AD1-1 | 164 604 | 0.7 | 2105 | 2.0 | 0.01 | 0.12 |
| Cont-PP-AD2-1 | 168 772 | 3.7 | 2205 | 4.5 | 0.01 | 0.11 |
| Cont-PP-AD3-1 | 164 170 | 2.3 | 2135 | 1.8 | 0.01 | 0.13 |
| Cont-PP-AD4-1 | 174 579 | 1.5 | 2376 | 2.4 | 0.01 | 0.09 |
| Cont-PP-AD5-1 | 178 625 | 1.6 | 2211 | 2.0 | 0.01 | 0.09 |
| PP-AD1-1 | 208 442 | 2.0 | 2779 | 1.9 | 0.01 | 0.09 |
| PP-AD2-1 | 209 924 | 1.9 | 2799 | 3.1 | 0.01 | 0.09 |
| PP-AD3-1 | 208 995 | 3.8 | 2607 | 3.0 | 0.01 | 0.10 |
| PP-AD4-1 | 205 896 | 3.5 | 2693 | 1.6 | 0.01 | 0.08 |
| PP-AD5-1 | 205 672 | 2.1 | 2842 | 2.6 | 0.01 | 0.09 |

TABLE 7B

| Sample Name | Poission's Ratio | Tensile Strength (psi) | % RSD | Strain at Break (in/in) | % RSD | Stress at Break (psi) |
|---|---|---|---|---|---|---|
| Cont-PP | 0.40 | 4251 | 0.7 | 10.0 | 5.4 | 3156 |
| Cont-PP-M10 | 0.44 | 4081 | 0.7 | 10.4 | 4.5 | 3512 |
| Cont-PP-AD1-1 | 0.40 | 4051 | 1.0 | 8.4 | 2.7 | 3143 |
| Cont-PP-AD2-1 | 0.44 | 4191 | 1.1 | 9.3 | 11.8 | 3149 |
| Cont-PP-AD3-1 | 0.40 | 4064 | 1.2 | 7.0 | 11.4 | 2650 |
| Cont-PP-AD4-1 | 0.40 | 4057 | 0.8 | 8.5 | 5.9 | 3112 |
| Cont-PP-AD5-1 | 0.38 | 4052 | 0.8 | 6.5 | 10.0 | 3030 |
| PP-AD1-1 | 0.40 | 4772 | 1.3 | 10.9 | 8.7 | 2954 |
| PP-AD2-1 | 0.38 | 4620 | 2.0 | 10.4 | 4.7 | 3654 |
| PP-AD3-1 | 0.42 | 4690 | 1.5 | 10.4 | 3.2 | 3446 |
| PP-AD4-1 | 0.43 | 4523 | 0.6 | 10.3 | 4.3 | 3602 |
| PP-AD5-1 | 0.42 | 4986 | 0.8 | 11.0 | 5.8 | 3652 |

In view of Tables 6A & 6B and Tables 7A & 7B, the following facts have been observed.

Antimicrobial agents and modified PP content in the formulation do not have significant effect on the mechanical properties of the polymer.

Compare to comparative samples or to Cont-PP-M10 samples without agents, modified PP containing samples with the same amount of agent content shows slightly higher stiffness (tensile and flex modulus). Compare to comparative samples without modified PP, for example 1% secant modulus of Cont-PP-AD1-1 sample without modified PP is ~20% lower than PP-AD1-1 sample. There is the same observation for all other additives based on Tensile and Flexural mechanical data.

Stiffness (tensile and flex modulus) increase can be explained by the fact that modified PP improved additive dispersion and interactions between polymer and additive surfaces.

Also, strain at break value, that can be used to assess brittleness behavior of the materials, indicates that modified PP containing samples maintain similar brittleness behavior as PP resins without antimicrobial agents, however as seen from above table strain at break value of comparative samples are lower than Cont-PP. This fact can be explained by incompatibility between polymer matrix and antimicrobial agents.

Mechanical Properties—Notched Izod Impact. Pendulum impact resistance of notched specimens were measured in accordance with ASTM D-256:2010 using a Dynatup POE2000 Pendulum Tester. Table 8 provides impact resistance.

TABLE 8

| Sample Name | Failure Type | Impact Resistance (ft-lbf/in) | % RSD |
|---|---|---|---|
| Cont-PP | Complete | 0.45 | 7.8 |
| Cont-PP-M10 | Complete | 0.47 | 8.0 |
| Cont-PP-AD1-1 | Complete | 0.41 | 8.6 |
| Cont-PP-AD2-1 | Complete | 0.40 | 6.4 |
| Cont-PP-AD3-1 | Complete | 0.41 | 3.3 |
| Cont-PP-AD4-1 | Complete | 0.47 | 13.7 |
| Cont-PP-AD5-1 | Complete | 0.44 | 10.6 |
| PP-AD1-1 | Complete | 0.46 | 6.7 |
| PP-AD2-1 | Complete | 0.50 | 7.1 |
| PP-AD3-1 | Complete | 0.51 | 8.3 |
| PP-AD4-1 | Complete | 0.48 | 5.2 |
| PP-AD5-1 | Complete | 0.51 | 4.6 |

Antimicrobial agents and modified PP content in the formulation do not have significant effect on the notched impact properties of the polymer.

Fourier Transform Infrared Spectroscopy (FTIR). FTIR spectras were collected in 3000-4000 $cm^{-1}$ range using 32 scans. At 3000-3500 $cm^{-1}$ IR range appearance of —OH groups are observed for modified PP containing samples. This fact once again indicates that composition of the inventive compositions are different from the control samples. Also, existence of —OH group in non-polar polymer matrix will increase dispersion and compatibility of antimicrobial agents.

Figure 3:
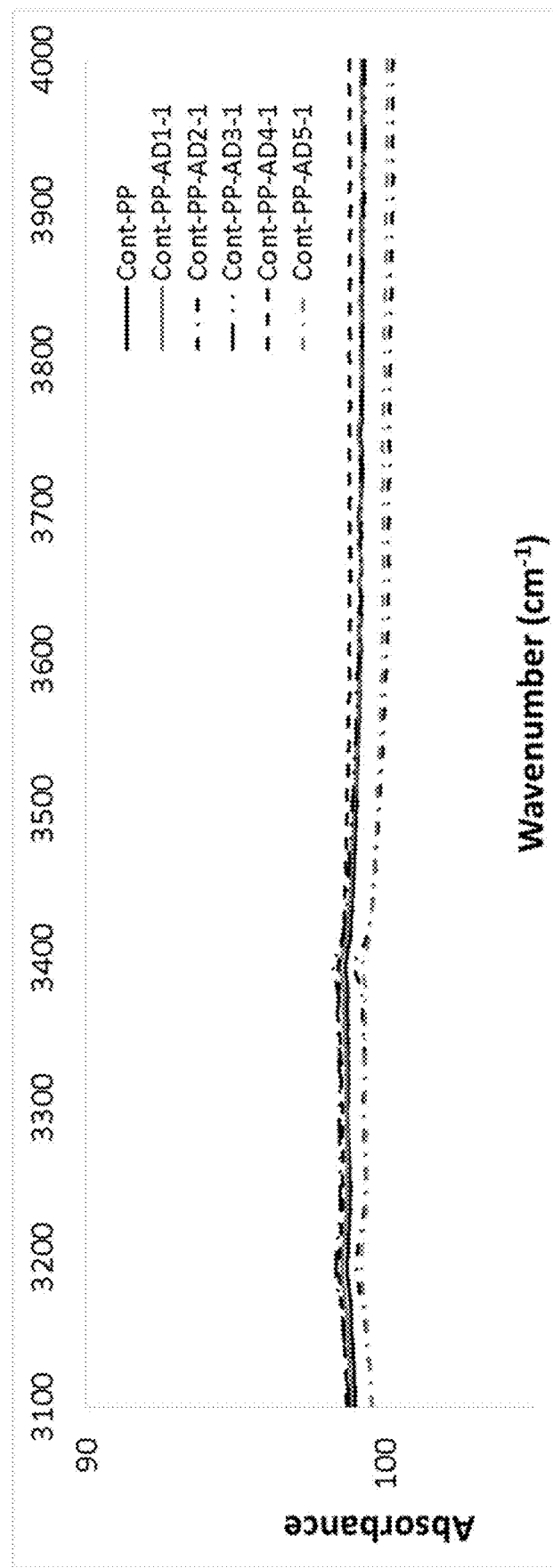
FIG. 3 provides FTIR spectra of control compositions: Group 1 "Cont-PP" and Group 2 of Table 3 in 3000 to 4000 $cm^{-1}$ range.
Figure 4:
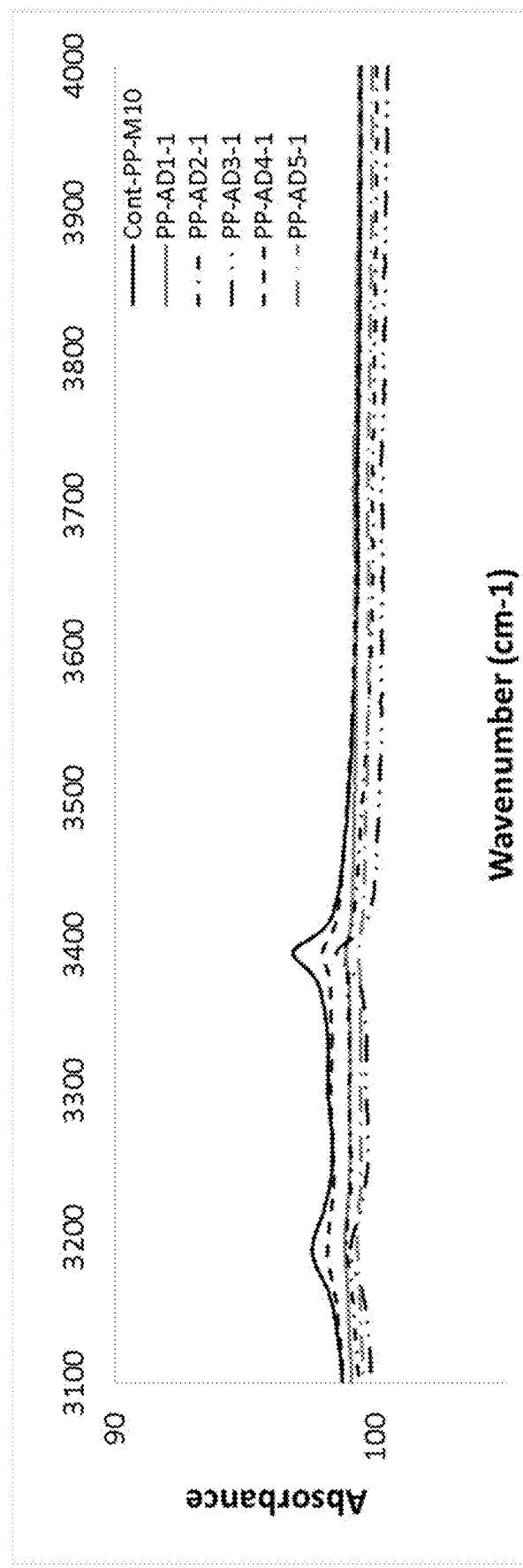
FIG. 4 provides a FTIR spectra of control composition Group 1 "Cont-PP-M10 and for the inventive compositions of Group 4 of Table 3 in 3000 to 4000 $cm^{-1}$ range.
Figure 5:
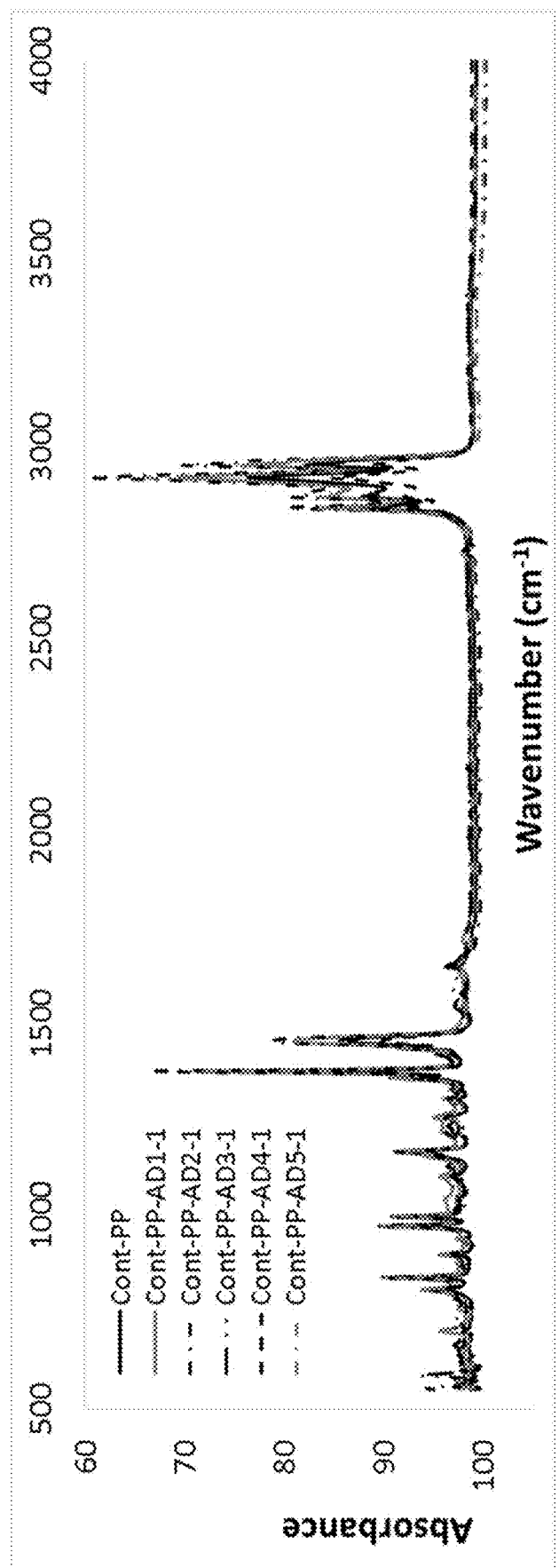
FIG. 5 provides FTIR spectra of control compositions: Group 1 "Cont-PP" and Group 2 of Table 3 in 500 to 4000 $cm^{-1}$ range.
Figure 6:
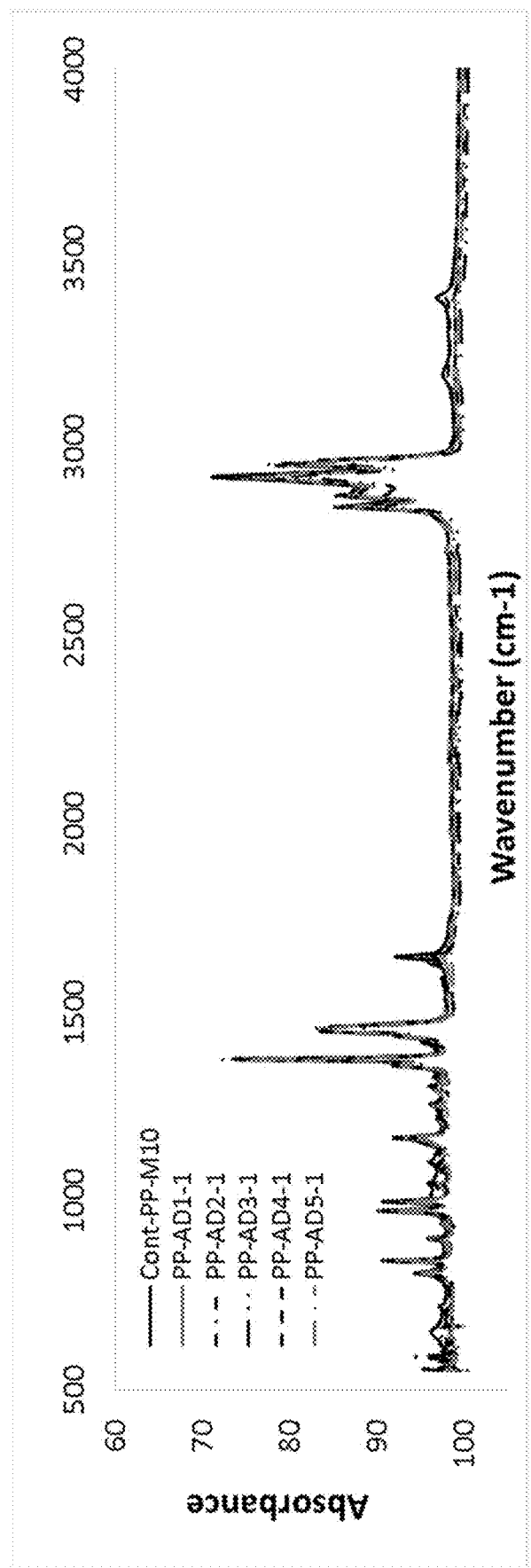
FIG. 6 provides a FTIR spectra of control composition Group 1 "Cont-PP-M10 and for the inventive compositions of Group 4 of Table 3 in 500 to 4000 $cm^{-1}$ range.
Figure 7:
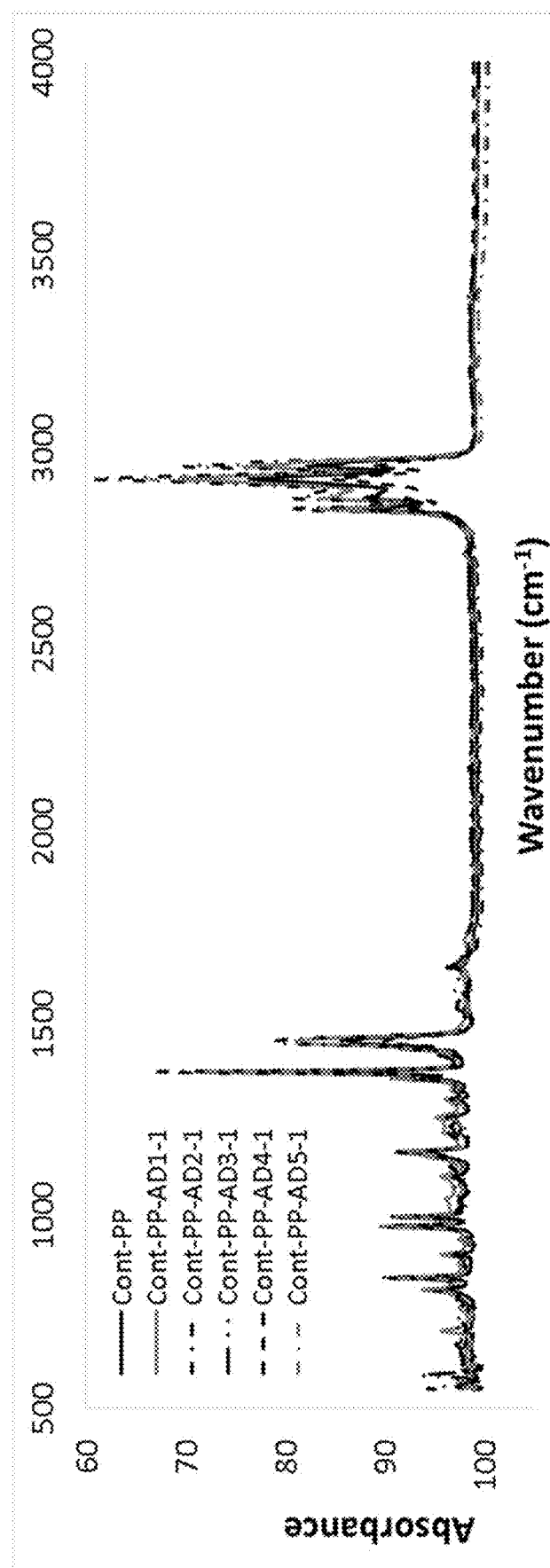
FIG. 7 provides FTIR spectra of control compositions: Group 1 "Cont-PP" and Group 2 of Table 3 in 540 to 1200 $cm^{-1}$ range.
Figure 8:
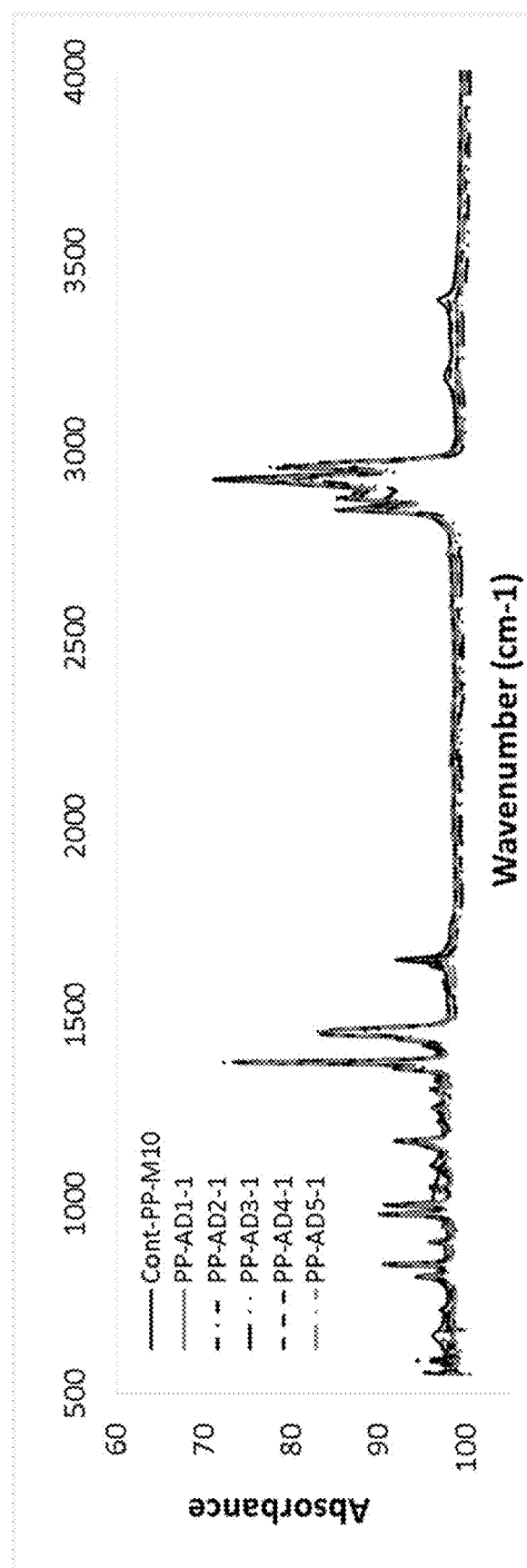
FIG. 8 provides a FTIR spectra of control composition Group 1 "Cont-PP-M10 and for the inventive compositions of Group 4 of Table 3 in 540 to 1200 $cm^{-1}$ range.

FIG. 3 provides FTIR spectra of control compositions: Group 1 "Cont-PP" and Group 2 of Table 3 in 3000 to 4000 cm-1 range; FIG. 4 provides a FTIR spectra of control composition Group 1 "Cont-PP-M10 and for the inventive compositions of Group 4 of Table 3 in 3000 to 4000 cm-1 range; FIG. 5 provides FTIR spectra of control compositions: Group 1 "Cont-PP" and Group 2 of Table 3 in 500 to 4000 cm-1 range; FIG. 6 provides a FTIR spectra of control composition Group 1 "Cont-PP-M10 and for the inventive compositions of Group 4 of Table 3 in 500 to 4000 cm-1 range; FIG. 7 provides FTIR spectra of control compositions: Group 1 "Cont-PP" and Group 2 of Table 3 in 540 to 1200 cm-1 range; FIG. 8 provides a FTIR spectra of control composition Group 1 "Cont-PP-M10 and for the inventive compositions of Group 4 of Table 3 in 540 to 1200 cm-1 range.

Antimicrobial Performance. Testing was done based on ISO 22196:2011, whose method specifies of evaluating the antibacterial activity of antibacterial-treated plastics, and other non-porous, surfaces of products (including intermediate products). Testing was done against two organisms: *Staphylococcus aureus* ATCC 6538 and *Pseudomonas aeruginosa* ATCC 9027. Concentration of bacteria was 2±0.5×105 CFU/ml. Bacteria survival was tested after 1, 3, and 24 hours of contact on a 50×50 mm polymer specimen surface.

Figure 9:
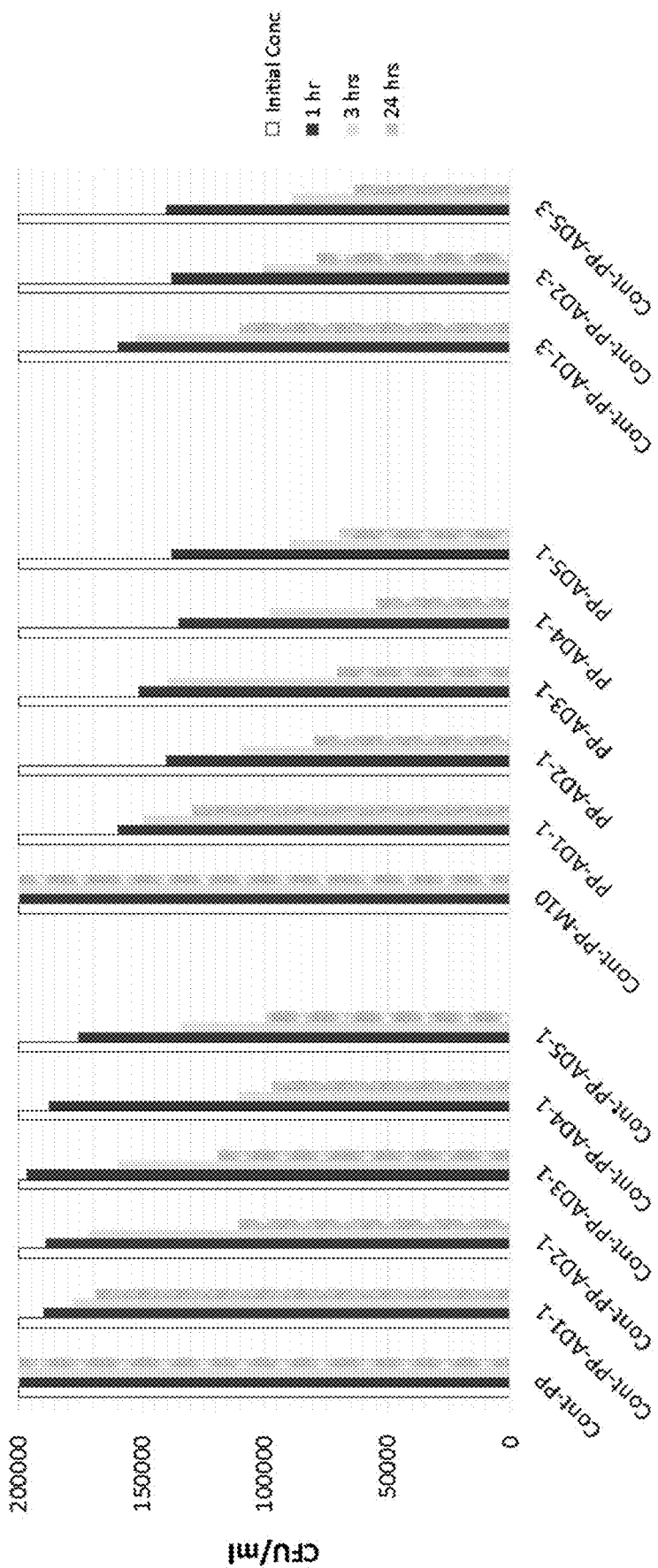
FIG. 9 provides a summary of antimicrobial performance of CFU/ml versus composition.

FIG. 9 provides a summary of antimicrobial performance of CFU/ml versus composition.

Figure 10:
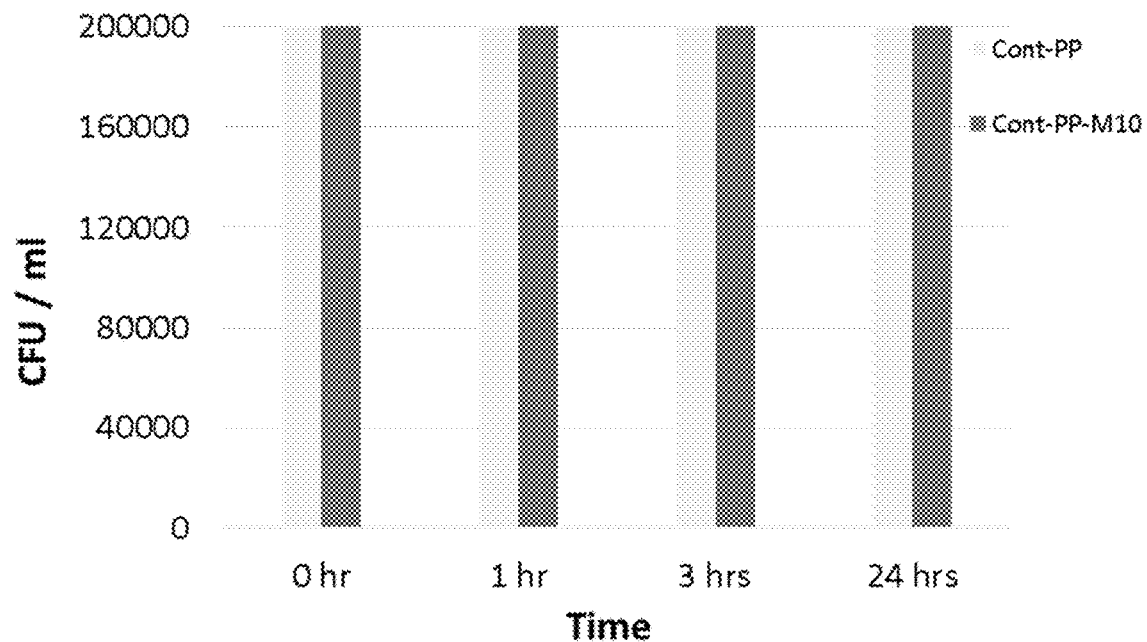
FIG. 10 provides a comparison of antimicrobial performance of CFU/ml versus time for control compositions without any antimicrobial agents: Cont-PP and Cont-PP-M10.

FIG. 10 provides a comparison of antimicrobial performance of CFU/ml versus time for control compositions without any antimicrobial agents: Cont-PP and Cont-PP-M10. Neither composition shows a decrease in bacteria concentration over time.

Figure 11:
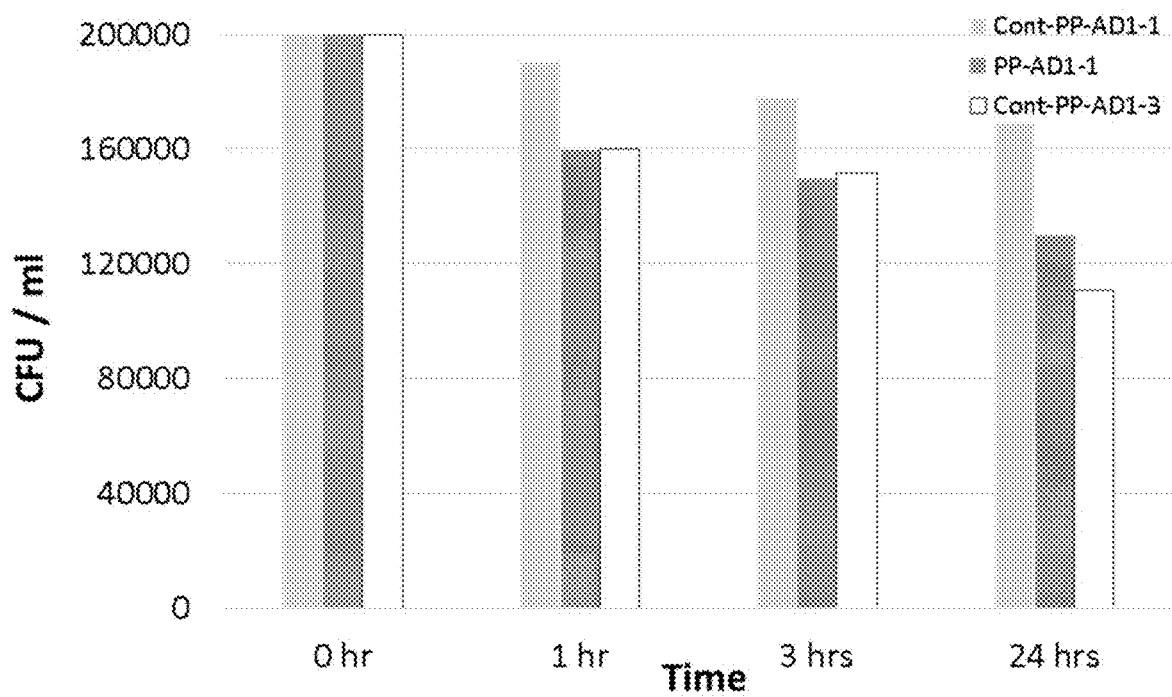
FIG. 11 provides a comparison of antimicrobial performance of CFU/ml versus time for inventive composition PP-AD1-1 with control compositions Cont-PP-AD1-1 and Cont-PP-AD1-3.

FIG. 11 provides a comparison of antimicrobial performance of CFU/ml versus time for inventive composition PP-AD1-1 with control compositions Cont-PP-AD1-1 and Cont-PP-AD1-3. The antimicrobial agent "AD1" is berberine chloride. Relative to the control composition at constant concentration of antimicrobial agent (Cont-PP-AD1-1), the inventive PP-AD1-1 showed lower bacteria count over time, which evidences enhanced antimicrobial properties. Relative to the control composition of higher concentration of antimicrobial agent (Cont-PP-AD1-3), the inventive PP-AD1-1 showed comparable performance over time, which indicates that the presence of the amphiphilic graft copolymer allows for use of less antimicrobial agent for similar performance.

Figure 12:
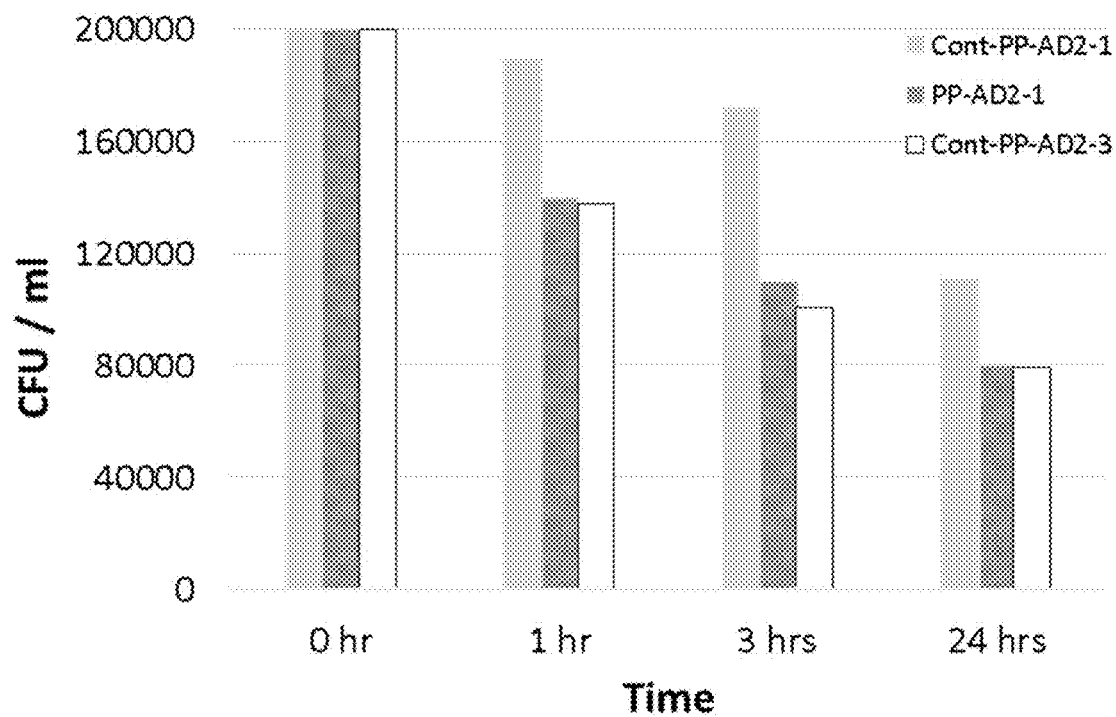
FIG. 12 provides a comparison of antimicrobial performance of CFU/ml versus time for inventive composition PP-AD2-1 with control compositions Cont-PP-AD2-1 and Cont-PP-AD2-3.

FIG. 12 provides a comparison of antimicrobial performance of CFU/ml versus time for inventive composition PP-AD2-1 with control compositions Cont-PP-AD2-1 and Cont-PP-AD2-3. The antimicrobial agent "AD2" is octinedine dihydrochloride. Relative to the control composition at constant concentration of antimicrobial agent (Cont-PP-AD2-1), the inventive PP-AD2-1 showed lower bacteria count over time, which evidences enhanced antimicrobial properties. Relative to the control composition of higher concentration of antimicrobial agent (Cont-PP-AD2-3), the inventive PP-AD1-1 showed comparable performance over time, which indicates that the presence of the amphiphilic graft copolymer allows for use of less antimicrobial agent for similar performance.

Figure 13:
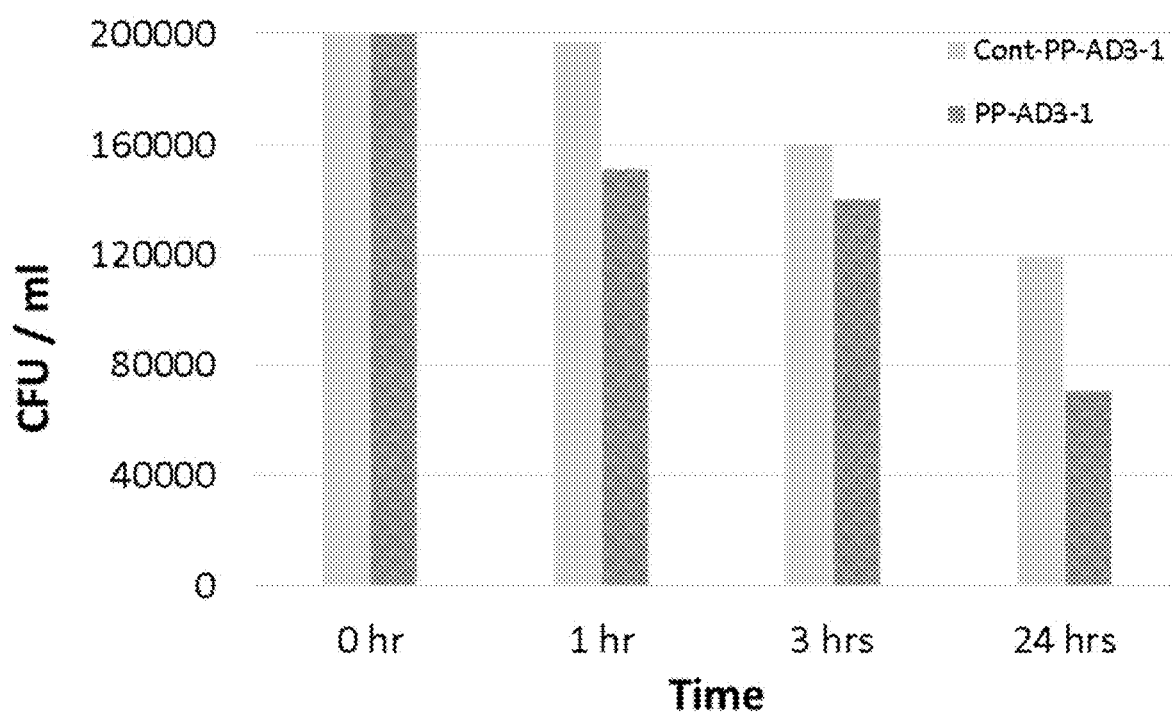
FIG. 13 provides a comparison of antimicrobial performance of CFU/ml versus time for inventive composition PP-AD3-1 with control composition Cont-PP-AD3-1.

FIG. 13 provides a comparison of antimicrobial performance of CFU/ml versus time for inventive composition PP-AD3-1 with control composition Cont-PP-AD3-1. The antimicrobial agent "AD3" is silver sulfadiazine. Relative to the control composition at constant concentration of antimicrobial agent (Cont-PP-AD3-1), the inventive PP-AD3-1 showed lower bacteria count over time, which evidences enhanced antimicrobial properties.

Figure 14:
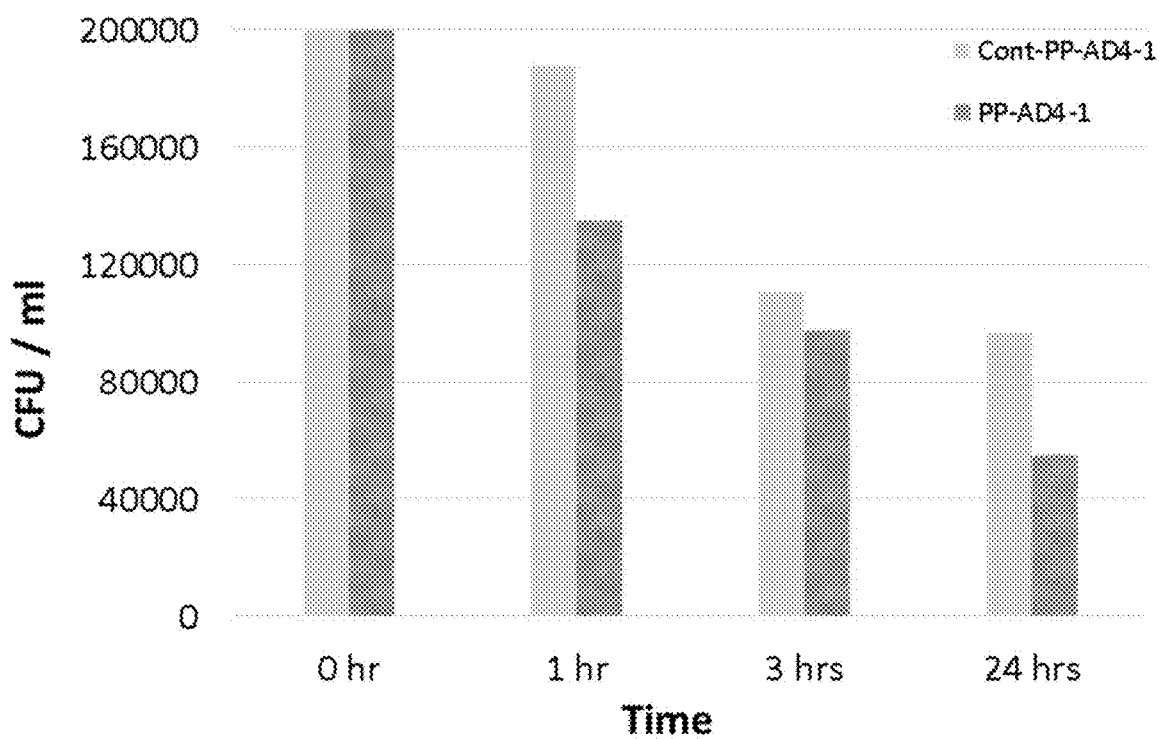
FIG. 14 provides a comparison of antimicrobial performance of CFU/ml versus time for inventive composition PP-AD4-1 with control composition Cont-PP-AD4-1.

FIG. 14 provides a comparison of antimicrobial performance of CFU/ml versus time for inventive composition PP-AD4-1 with control composition Cont-PP-AD4-1. The antimicrobial agent "AD4" is copper. Relative to the control composition at constant concentration of antimicrobial agent (Cont-PP-AD4-1), the inventive PP-AD4-1 showed lower bacteria count over time, which evidences enhanced antimicrobial properties.

Figure 15:
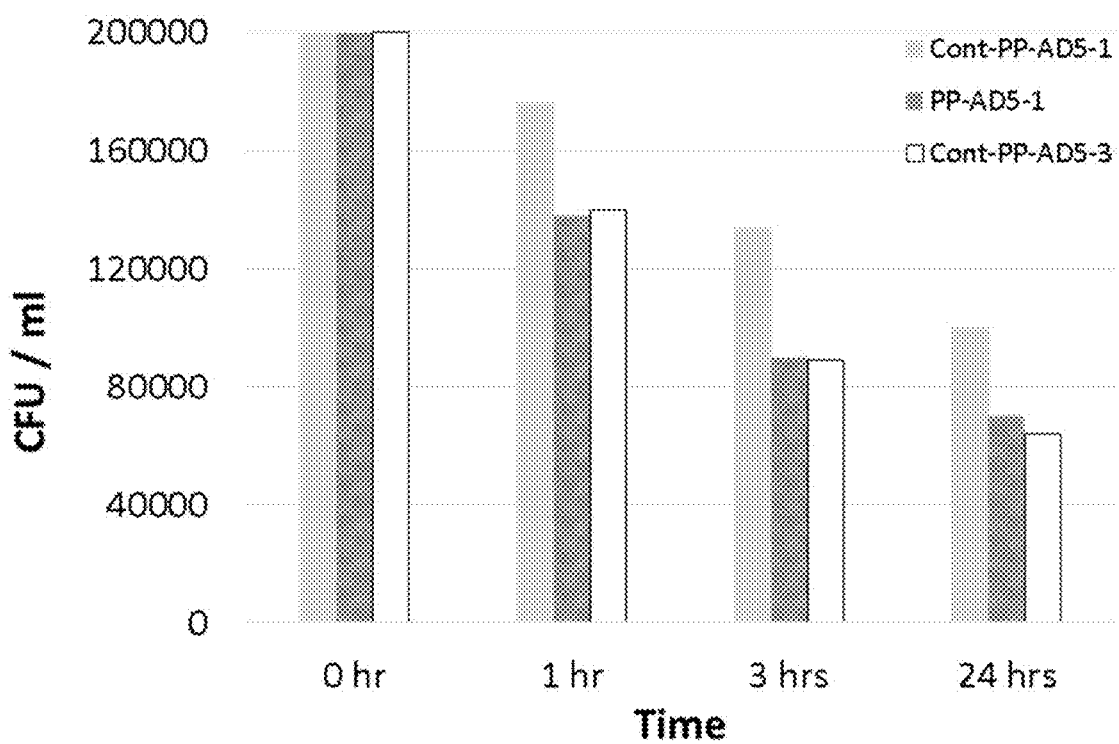
FIG. 15 provides a comparison of antimicrobial performance of CFU/ml versus time for inventive composition PP-AD5-1 with control compositions Cont-PP-AD5-1 and Cont-PP-AD5-3.

FIG. 15 provides a comparison of antimicrobial performance of CFU/ml versus time for inventive composition PP-AD5-1 with control compositions Cont-PP-AD5-1 and Cont-PP-AD5-3. The antimicrobial agent "AD5" is silver. Relative to the control composition at constant concentration of antimicrobial agent (Cont-PP-AD5-1), the inventive PP-AD5-1 showed lower bacteria count over time, which evidences enhanced antimicrobial properties. Relative to the control composition of higher concentration of antimicrobial agent (Cont-PP-AD5-3), the inventive PP-AD1-1 showed comparable performance over time, which indicates that the presence of the amphiphilic graft copolymer allows for use of less antimicrobial agent for similar performance.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical device comprising:
    a polymeric body comprising:
    a base polymeric formulation comprising a polymer or co-polymer of propylene; and
    an additive comprising a PP-g-XSiOA copolymer having a polypropylene backbone and hybrid micromolecule side-chains based on organo-functional silanes;
    the PP-g-XSiOA copolymer being in a blend with the base polymeric formulation in an amount in the range of about 0.01 to about 20.0% by weight of the blend; and
    an antimicrobial agent;
    wherein the PP-g-XSiOA copolymer is according to Formula (I):

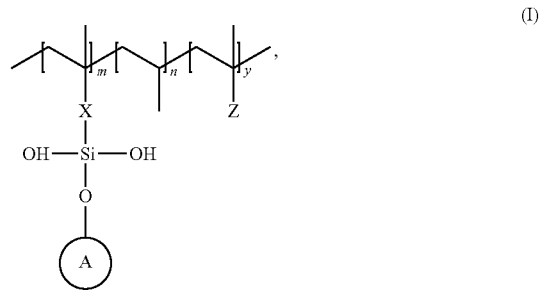

(I)

wherein "X" is an organic group or an organo-functional group; "A" is a metal, an inorganic oxide, an inorganic hydroxide, or any other inorganic material; "n" is in the range of about 78 to 99.9 mole percent; "m" is in the range of about 0.1 to 20 mole percent; "y" is in the range of 0 to 2.0 mole percent; and "Z", when "y" is greater than 0, comprises: $M-X_2$; XSiOR; or XSiOH, wherein "M-X$_2$" is an organo-metal salt and "OR" is an alkoxy group having 1 to 4 carbons.

2. The medical device of claim 1, wherein the antimicrobial agent comprises: berberine chloride, berberine chloride hydrate, octinedine dihydrochloride, 4-chlorophenyl methyl sulfone, climbazole, piroctone olamine, silver sulfadiazine, copper particles, silver particles, or combinations thereof.

3. The medical device of claim 2, wherein the antimicrobial agent is present in an amount in the range of 0.02 to 3% by weight of the blend of additive and base polymeric formulation.

4. The medical device of claim 1, wherein the base polymeric formulation comprises polypropylene, a polyethylene-polypropylene co-polymer, a polypropylene-containing thermoplastic elastomer (TPE), or combinations thereof.

5. The medical device of claim 1, wherein X of the PP-g-XSiOA copolymer is derived from a compound selected from the group consisting of epoxy, amino, acrylate, methacryloxy, and vinyl; and A is selected from the group consisting of: silicon (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

6. The medical device of claim 1, wherein the PP-g-XSiOA copolymer has a melting point in the range of 140 to 180° C.

7. The medical device of claim 1, wherein the PP-g-XSiOA copolymer has a capillary viscosity in the range of 100 to 300 Pa·s at 180 s$^{-1}$.

8. The medical device of claim 1, wherein the PP-g-XSiOA copolymer has a weight average molecular weight (Mw) in the range of about 100,000 to about 350,000 g/mol.

9. The medical device of claim 1, wherein the PP-g-XSiOA copolymer has a dispersity index in the range of 1.5 to 9.

10. The medical device of claim 1, wherein the PP-g-XSiOA copolymer has a long chain branching frequency in the range of 0.007 to 0.017 per 1000 carbon.

11. The medical device of claim 1, wherein the PP-g-XSiOA copolymer has a melt flow rate in the range of 15 to 55 g/10 minutes.

12. The medical device of claim 1 in the form of tubing, barrel, rod, or any other geometric shape.

13. A method of making a medical device comprising:
obtaining a PP-g-XSiOA copolymer having a polypropylene backbone and hybrid micromolecule side-chains based on organo-functional silanes;
combining the PP-g-XSiOA copolymer with a base polymeric formulation comprising a polymer or co-polymer of propylene to form a blend, the PP-g-XSiOA copolymer being present in the blend in an amount in the range of about 0.01 to about 20.0% by weight of the blend;
adding an antimicrobial agent to the blend to form a mixture; and
forming a polymeric body from the mixture;
wherein the PP-g-XSiOA copolymer is according to Formular (I):

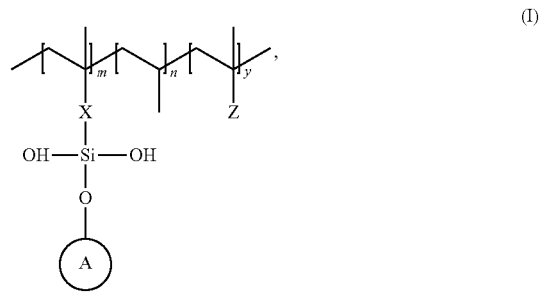

wherein "X" is an organic group or an organo-functional group; "A" is a metal, an inorganic oxide, an inorganic hydroxide, or any other inorganic material; "n" is in the range of about 78 to 99.9 mole percent; "m" is in the range of about 0.1 to 20 mole percent; "y" is in the range of 0 to 2.0 mole percent; and "Z", when "y" is greater than 0, comprises: M-X$_2$; XSiOR; or XSiOH, wherein "M-X$_2$" is an organo-metal salt and "OR" is an alkoxy group having 1 to 4 carbons.

14. The method of claim 13, wherein the antimicrobial agent comprises: berberine chloride, berberine chloride hydrate, octinedine dihydrochloride, 4-chlorophenyl methyl sulfone, climbazole, piroctone olamine, silver sulfadiazine, copper particles, silver particles, or combinations thereof.

15. The method of claim 13, wherein the base polymeric formulation comprises polypropylene, a polyethylene-polypropylene co-polymer, a polypropylene-containing thermoplastic elastomer (TPE), or combinations thereof.

16. The method of claim 13, wherein X of the PP-g-XSiOA copolymer is derived from a compound selected from the group consisting of epoxy, amino, acrylate, methacryloxy, and vinyl; and A is selected from the group consisting of: silicon (Si), aluminum (Al), iron (Fe), titanium (Ti), silver (Ag), zinc (Zn), nickel (Ni), calcium (Ca), copper (Cu), tin (Sn); oxides thereof; hydroxides thereof; and mixtures of the foregoing.

17. The method of claim 13, wherein the medical device is in the form of tubing, barrel, rod, or any other geometric shape.

* * * * *